US012576187B2

(12) United States Patent
Popat et al.

(10) Patent No.: US 12,576,187 B2
(45) Date of Patent: Mar. 17, 2026

(54) ANTIADHESIVE SUPERHYDROPHOBIC SURFACES

(71) Applicant: COLORADO STATE UNIVERSITY RESEARCH FOUNDATION, Fort Collins, CO (US)

(72) Inventors: Ketul C. Popat, Fort Collins, CO (US); Vignesh Kannigaipair Manivasagam, Fort Collins, CO (US)

(73) Assignee: COLORADO STATE UNIVERSITY RESEARCH FOUNDATION, Fort Collins, CO (US)

( * ) Notice: Subject to any disclaimer, the term of this patent is extended or adjusted under 35 U.S.C. 154(b) by 652 days.

(21) Appl. No.: 18/047,152

(22) Filed: Oct. 17, 2022

(65) Prior Publication Data

US 2024/0123118 A1     Apr. 18, 2024

(51) Int. Cl.
*A61L 27/30* (2006.01)
*A61L 27/50* (2006.01)
(Continued)

(52) U.S. Cl.
CPC ............. *A61L 27/306* (2013.01); *A61L 27/50* (2013.01); *A61L 31/088* (2013.01); *A61L 31/10* (2013.01); *B82Y 30/00* (2013.01); *A61L 2400/12* (2013.01); *A61L 2400/18* (2013.01); *A61L 2420/02* (2013.01); *A61L 2420/04* (2013.01); *A61L 2420/08* (2013.01)

(58) Field of Classification Search
CPC ...... A61L 27/306; A61L 27/50; A61L 31/088; A61L 31/10; A61L 2400/12; A61L 2400/18; A61L 2420/02; A61L 2420/04; A61L 2420/08; A61L 27/06; A61L 33/0094; A61L 2430/20; B82Y 30/00
See application file for complete search history.

(56) References Cited

U.S. PATENT DOCUMENTS 6,183,255 B1    2/2001  Oshida
7,501,073 B2    3/2009  Wen et al.
(Continued)

OTHER PUBLICATIONS

Bartlet et al., Superhemophobic titania nanotube array surfaces for blood contacting medical devices, RSC Adv., 2017, 7, pp. 35466-35476.
(Continued)

*Primary Examiner* — Michael B Nelson
(74) *Attorney, Agent, or Firm* — Haukaas Fortius PLLC; Michael Haukaas

(57) ABSTRACT

A titanium superhydrophobic surface comprising a coating of a perfluorosilane on contiguous titania micrograins surrounded by crevices, the micrograins comprising a topography of nanopits shaped by contiguous peaks and valleys. The superhydrophobic surface has significantly increased hemocompatibility and enhanced antibacterial properties compared to an unmodified titanium surface. The increased hemocompatibility was confirmed by reduced platelet adhesion, reduced leukocyte adhesion, and reduced thrombus formation. The surface is prepared by a facile hydrothermal treatment of a titanium surface with sulfuric acid, leading to the formation of a unique micro-nano surface topography. The superhydrophobic surface was then achieved by coating the micro-nano titanium surface with a low energy silane using physical vapor deposition.

20 Claims, 28 Drawing Sheets

(51) Int. Cl.
    *A61L 31/08*        (2006.01)
    *A61L 31/10*        (2006.01)
    *B82Y 30/00*       (2011.01)

(56)             References Cited

U.S. PATENT DOCUMENTS

| | | |
|---|---|---|
| 8,221,639 B2 | 7/2012 | Towse et al. |
| 8,641,418 B2 | 2/2014 | Mayfield et al. |
| 9,642,708 B2 | 5/2017 | Fredriksson et al. |

OTHER PUBLICATIONS

Chenab et al., "Superhydrophobicity: advanced biological and biomedical applications", Biomater. Sci., 2019, 7, pp. 3110-3137.

Huang et al., Hemocompatibility of titanium oxide films, Biomaterials 24, Jun. 2003, vol. 24, Issue 13, pp. 2177-2187.

Jokinen et al., "Superhydrophobic Blood-Repellent Surfaces", Adv. Mater. 2018, 30, 1705104, 10pgs.

Li et al., "Biomimetic superhydrophobic and antibacterial stainless-steel mesh via double-potentiostatic electrodeposition and modification", Surface & Coatings Technology, Dec. 15, 2020, vol. 403, I26355, 9pgs.

Maitz et al., "Blood Compatibility of Titanium Oxides with Various Crystal Structure and Element Doping", Journal of Biomaterials Applications, Apr. 2003, vol. 17, pp. 303-319.

Manivasagam et al., "Enhanced antibacterial properties on superhydrophobic micro-nano structured titanium surface", J Biomed Mater Res. 2022; Feb. 21, 2022, vol. 110, Issue 7, pp. 1314-1328.

Manivasagam et al., "In Vitro Investigation of Hemocompatibility of Hydrothermally Treated Titanium and Titanium Alloy Surfaces", ACS Omega 2020, 5, 8108-8120.

Manivasagam et al., "Surface modification strategies to improve titanium hemocompatibility: a comprehensive review", Mater. Adv., 2021, 2, pp. 5824-5842.

Manivasagam et al., Hydrothermally treated titanium surfaces for enhanced osteogenic differentiation of adipose derived stem cells, Materials Science & Engineering: C, Sep. 2021, vol. 128, 112315, 13pgs.

Montgomerie et al., Improved hemocompatibility and reduced bacterial adhesion on superhydrophobic titania hanoflower surfaces, Materials Science & Engineering: C, vol. 119, Feb. 2021, 111503, 15pgs.

Movafaghi et al., "Hemocompatibility of Superhemophobic Titania Surfaces", Adv. Healthcare Mater. 2017, Dec. 21, 2016, 6, 1600717, 6pgs.

Sabino et al., "Enhanced hemocompatibility and antibacterial activity on titania nanotubes with tanfloc/heparin bolyelectrolyte multilayers", J Biomed Mater Res. 2020; 108:992-1005.

Sabino et al., "Improved in vitro endothelialization on nanostructured titania with tannin/glycosaminoglycan-based bolyelectrolyte multilayers", In vitro models 1, Jun. 3, 2022, pp. 249-259.

Sabino et al., "Interaction of blood plasma proteins with superhemophobic titania nanotube surfaces", Nanomedicine: Nanotechnology, Biology, and Medicine 21, Oct. 2019, vol. 21, 102046, 11pgs.

Sabino et al., "Tanfloc/heparin polyelectrolyte multilayers improve osteogenic differentiation of adipose-derived stem cells on titania nanotube surfaces", Carbohydrate Polymers 251, Jan. 2021, 117079, 10pgs.

Sikka et al., "The role of biopolymers and biodegradable polymeric dressings in managing chronic wounds", Advanced Textiles for Wound Care, 2019, pp. 463-488.

Tavares et al., "Treatment of a commercial, machined surface titanium implant with H2SO4/H2O2 enhances contact osteogenesis", Clin. Oral Impl. Resp., 18, Aug. 2007, pp. 452-458.

Tuteja et al., "Robust omniphobic surfaces", PNAS, Nov. 25, 2008, vol. 105, No. 47, pp. 18200-18205.

Vanithakumari et al., "Fabrication of superhydrophobic titanium surfaces with superior antibacterial properties using graphene oxide and silanized silica nanoparticles", Surface & Coatings Technology, Oct. 25, 2020, vol. 400, I26074; 16pgs.

Virk et al., "Erythrocyte interaction with titanium nanostructured surfaces", In vitro models, Aug. 31, 2022, 17pgs.

Vishnu et al., "Hydrothermal treatment of etched titanium: A potential surface nano-modification technique for enhanced biocompatibility", Nanomedicine: Nanotechnology, Biology, and Medicine 20, Aug. 2019, vol. 20, 102016, 10pgs.

b)

c)

b)

c)

b)

c)

ANTIADHESIVE SUPERHYDROPHOBIC SURFACES

GOVERNMENT SUPPORT

This invention was made with government support under grant R01 HL135505 and R21 HL139208 awarded by National Institutes of Health. The government has certain rights in the invention.

BACKGROUND OF THE INVENTION

Implantable medical devices such as cardiovascular or orthopedic implants are commonly used in patients to improve quality of life by replacing damaged human tissue. In the United States alone, more than three million orthopedic implants and one million cardiac implants surgeries are performed annually. These numbers are expected to increase due to the availability of advanced surgical procedures and increased average life expectancy across all age groups. Despite many advances in surgical procedures, infection remains a major cause of implant failure.

Almost 25% of health care associated infections in the United States are implant-related infections. Implant-associated infections involve complex interactions between the implant surface, pathogenic bacteria, and the patient's immune system. The human immune response is normally strong enough to clear infectious bacteria. However, after bacteria adhere to an implant surface, they can proliferate and form a protective biofilm that shields the bacteria from antibiotic treatments. The Centers for Disease Control and Prevention (CDC) and the National Institutes of Health (NIH) estimate that biofilm phenotype bacteria cause 65 to 80% of all human infectious diseases. Accordingly, there is a need for implant surfaces that inhibit the formation of biofilms.

Studies have also shown that an overuse of antibiotics has resulted in the development of numerous forms of antibiotic resistant strains of bacteria. Some bacteria have even developed tolerance against ethanol-based disinfectants. As a result, implant infections have become increasingly difficult to treat. New implant materials with antibacterial properties are therefore needed to reduce infections related to biomedical implants.

Furthermore, although titanium and its alloys have been a preferred choice of material for cardiovascular implants, the metal of these implants have been associates with blood coagulation cascades followed by thrombus formation and inflammation. Several approaches have been investigated to develop cardiovascular implant surfaces with improved blood compatibility. One technique, surface passivation, can provide a hydrophilic surface having improved hemocompatibility. However, while hydrophilic surfaces have proven advantageous for some implants, they can also increase the risk of thrombus formation.

Because procedures involving biomedical implants are prone to cause bacterial infections and blood clotting, there is a need for new implant materials with surfaces that reduce biofilm formation, inhibit implant infections, and reduce patient susceptibility to clotting.

SUMMARY

The technology disclosed herein provides a superhydrophobic surface that, when used in a biomedical implant, reduces biofilm formation, inhibits implant infections, and reduces patient susceptibility to blood clots. The superhydrophobic surface comprises a coating of a perfluorosilane on contiguous titania micrograins surrounded by crevices, the micrograins comprising a topography of nanopits shaped by contiguous peaks and valleys. The average longest length of the micrograins is between 6 μm and 16 μm, and the average diameter of the nanopits is between 400 nm and 1,000 nm. The surface has a high oxygen content, typically an oxygen to carbon ratio of about 2:1, based on XPS analysis, while still maintaining superhydrophobic properties.

To prepare the superhydrophobic surface with enhanced antibacterial activity and blood compatibility, an innovative hydrothermal treatment was used modify the surface morphology and chemistry of a titanium surface. A sulfuric acid hydrothermal etching treatment of a plain titanium surface led to a surface with micro-nano topography. Upon further modification with silane, the surface became superhydrophobic. The three-dimensional micro features were developed as a result of faster etching at grain boundaries compared to grain centers and the titania grains were simultaneously etched in a unidirectional manner, creating nanopits, which in combination resulted in a novel micro-nano surface morphology. Compared to an unmodified titanium surface, the superhydrophobic micro-nano structured titanium surface significantly reduced bacteria cell adhesion (>90%) and prevented biofilm formation after 24 hours of incubation. The superhydrophobic micro-nano structured titanium surface also showed improved hemocompatibility, significantly reducing fibrinogen adsorption, and platelet and leukocyte adhesion and activation. Accordingly, the surface can be used as a biomedical implant.

The disclosed technology also a method for fabricating an antiadhesive superhydrophobic surface comprising:
  a) etching a plain titanium surface using sulfuric acid under a controlled temperature and time of exposure to form a hydrothermally treated surface;
  b) annealing the hydrothermally treated surface;
  c) etching the annealed surface with oxygen plasma; and
  d) fluorinating the etched surface with a perfluorosilane to form an antiadhesive superhydrophobic surface. The antiadhesive superhydrophobic surface can be incorporated into a device for use as a biomedical implant.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

3 for carbon peaks on different surfaces. XPS was performed on at least 3 different substrates of each surface (n min=9).

Figure 4:
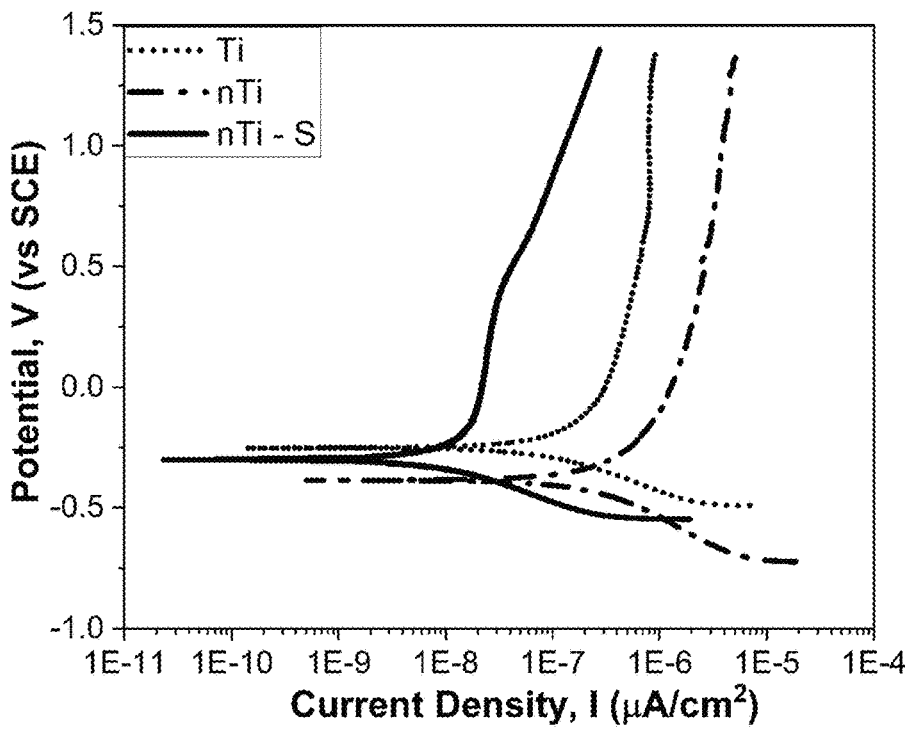

FIG. 4. Cyclic polarization curves for different surfaces. Potentiodynamic tests were d performed one on at least 3 different substrates of each surface ($n_{min}$=3).

Figure 5:
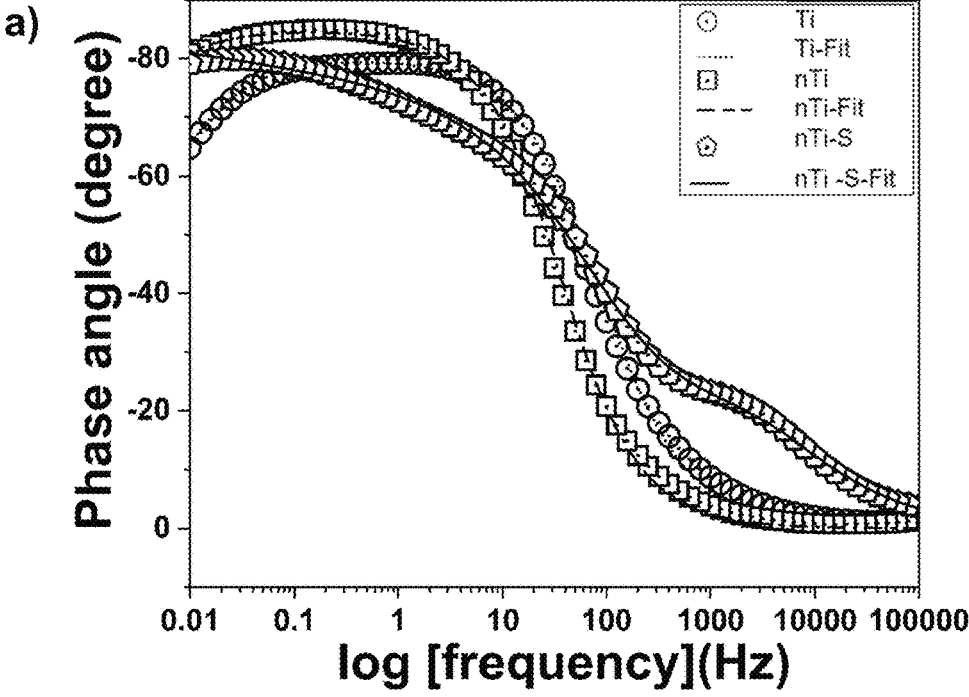
Figure 5:
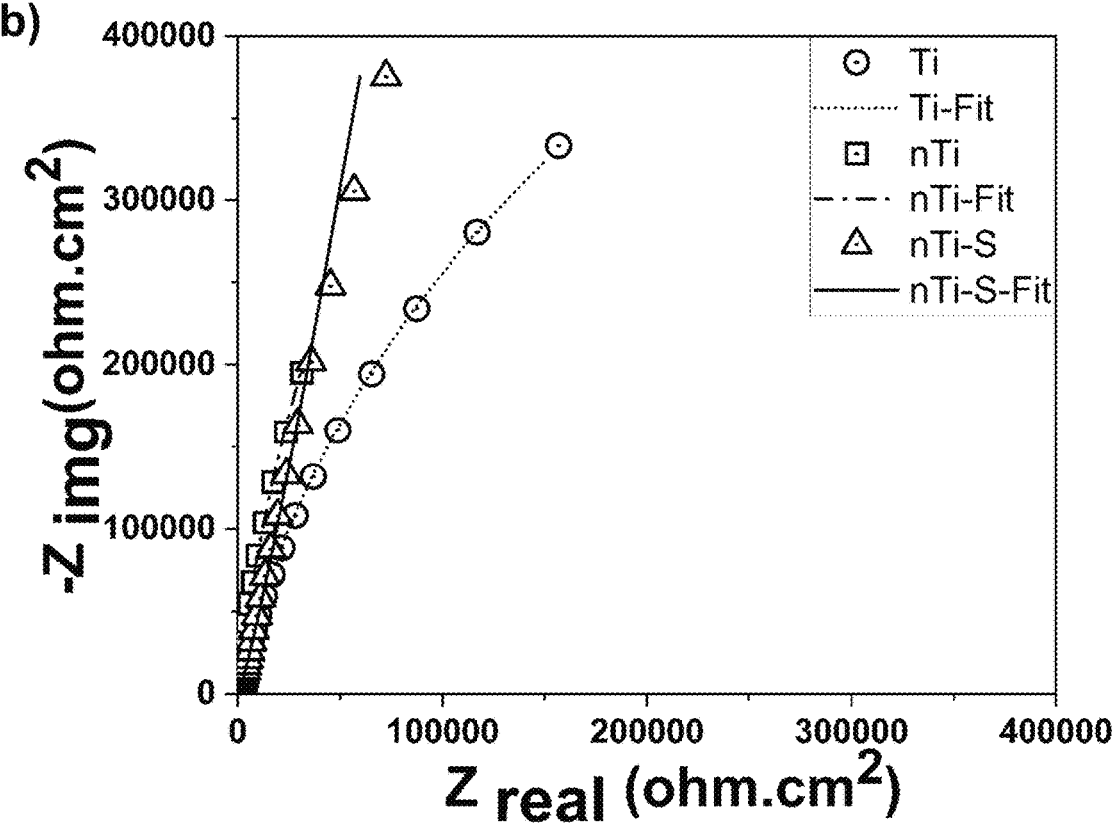
Figure 5:
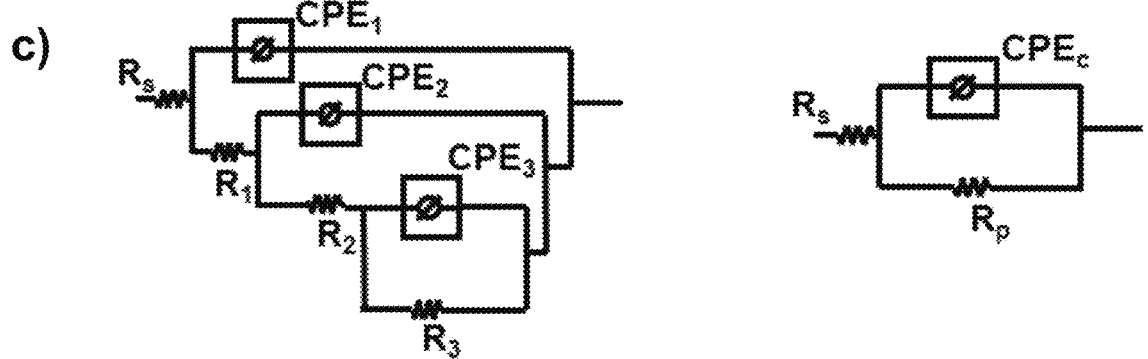

FIG. 5. a) Nyquist plot and b) Bode plot for different surfaces. c) Equivalent electrical circuit for two different cases.

Figure 6:
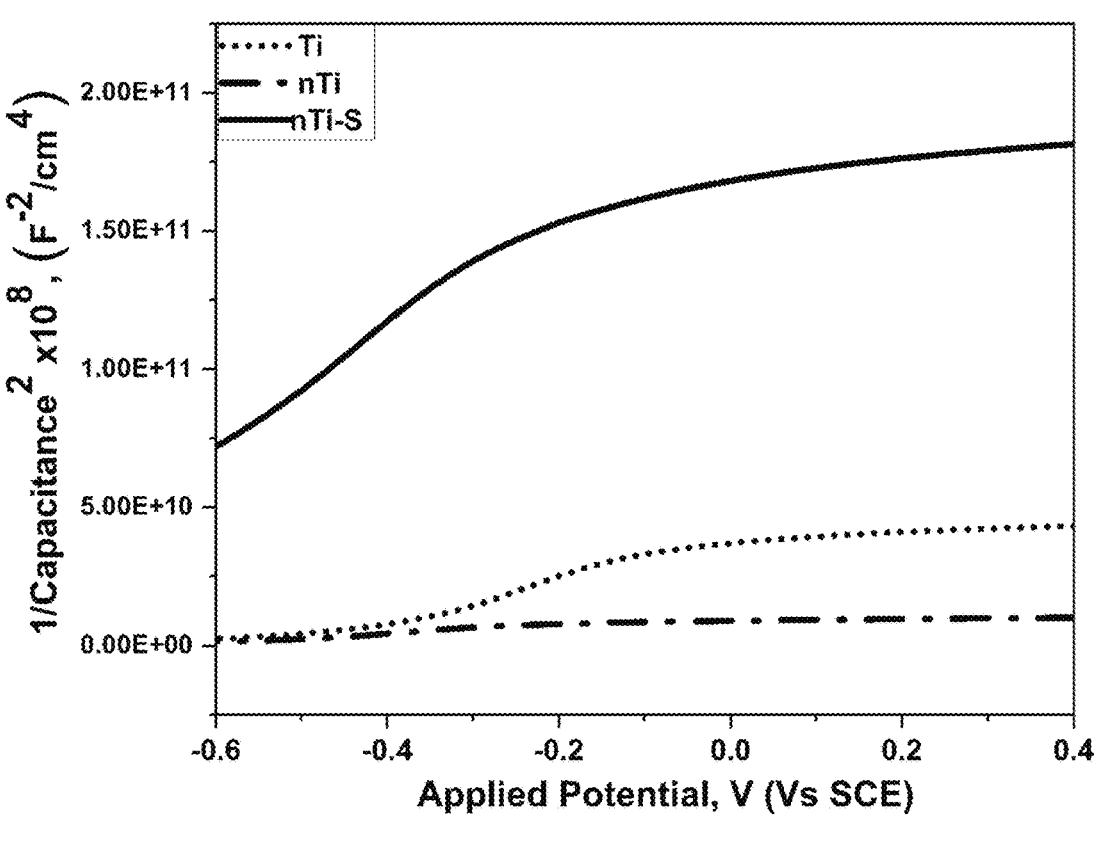

FIG. 6. Mott Schottky curves of different surfaces.

Figure 7:
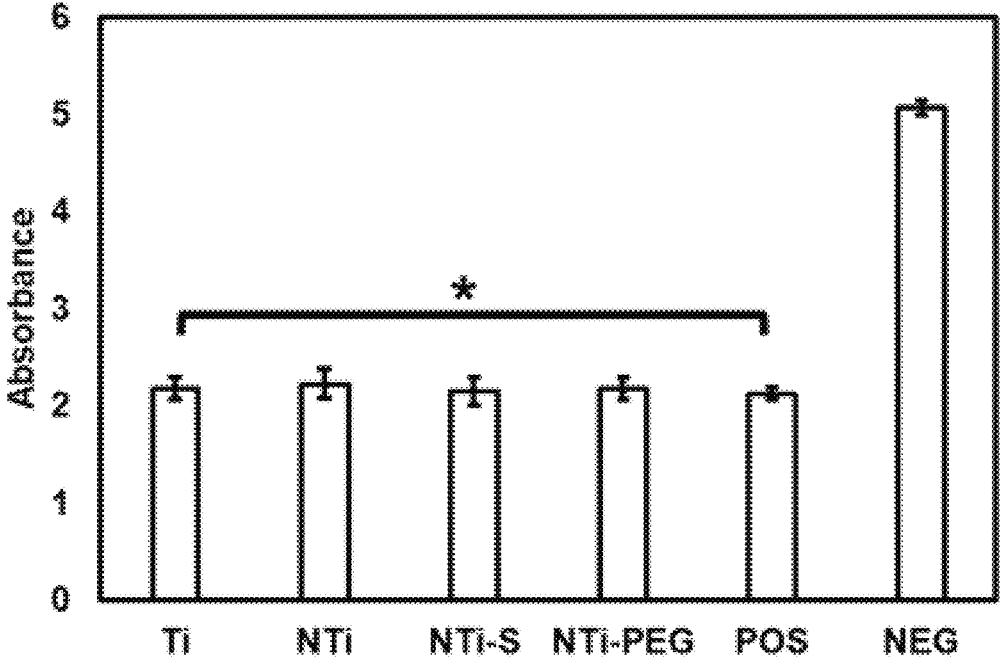

FIG. 7. Cell cytotoxicity of platelet rich plasma (PRP) exposed different surfaces measured using the LDH assay. *p<0.05 indicates statistical significance. The error bar represents the standard deviation. Cell cytotoxicity tests were performed on at least 6 different substrates of each surface ($n_{min}$=6).

Figure 8:
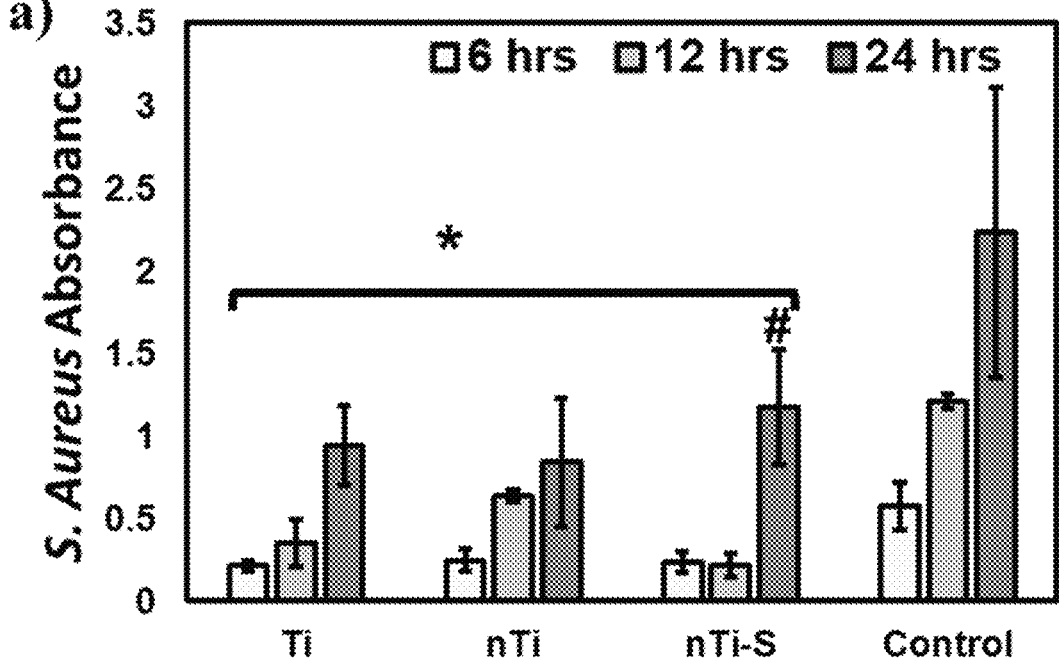
Figure 8:
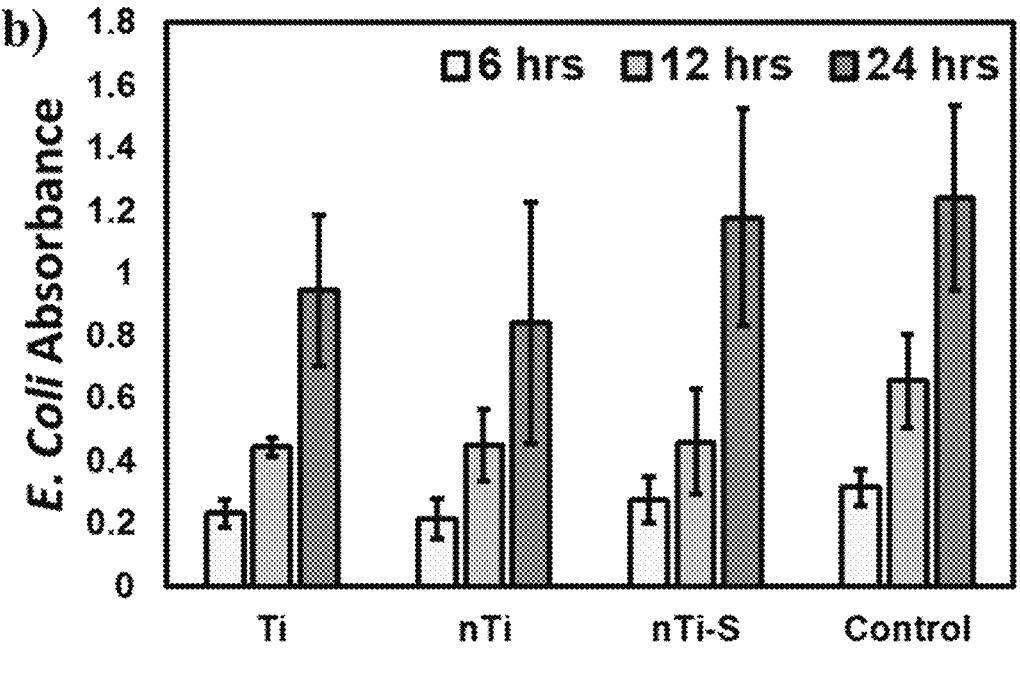

FIG. 8. Inhibition of a) *S. aureus* and b) *E. coli* growth in the media by different surfaces. *p<0.05 indicates statistical significance, #p>0.05 indicates no statistical significance. The error bar represents the standard deviation. Bacterial inhibition studies were performed on at least 9 different substrates of each surface ($n_{min}$=9).

Figure 9:
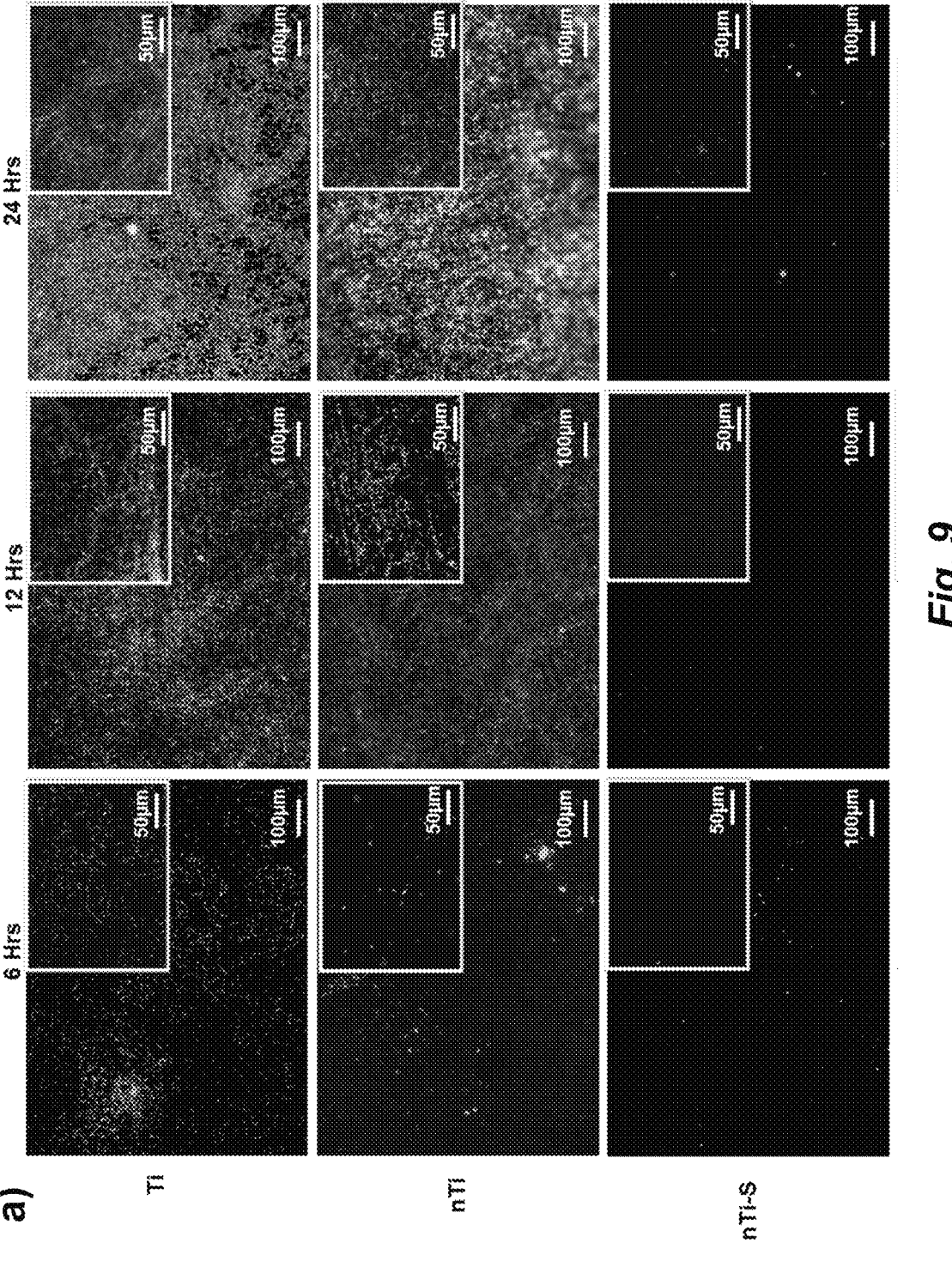
Figure 9:
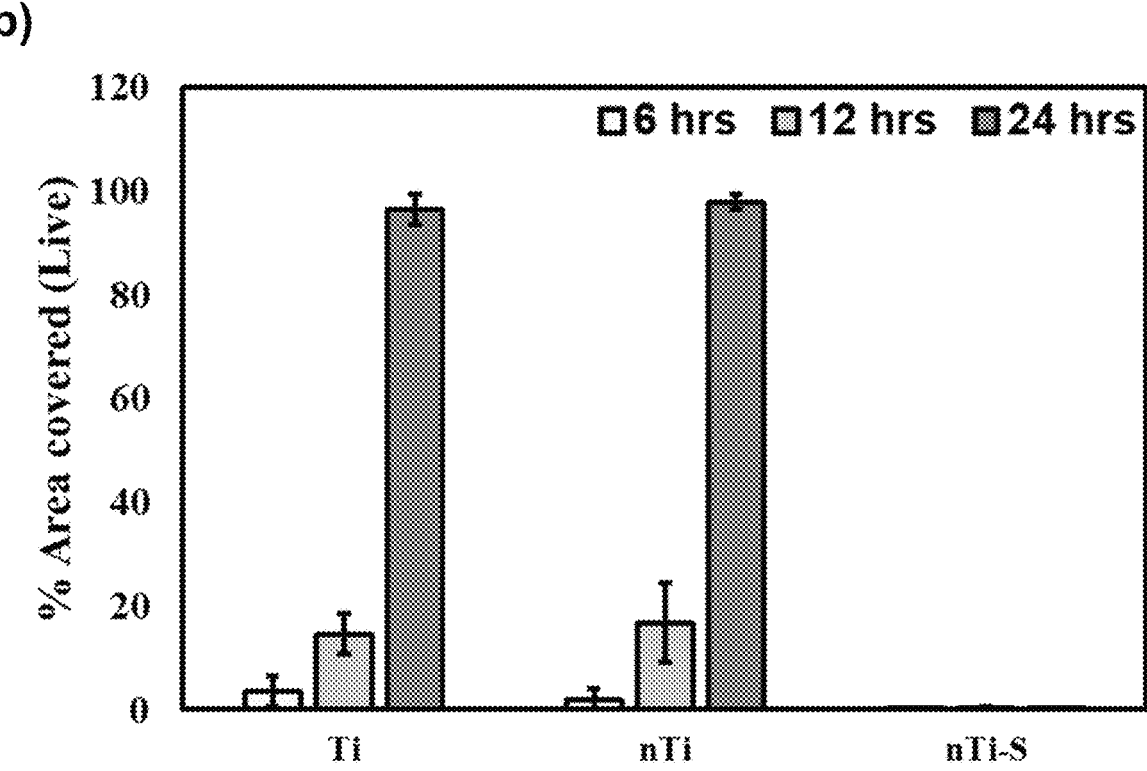
Figure 9:
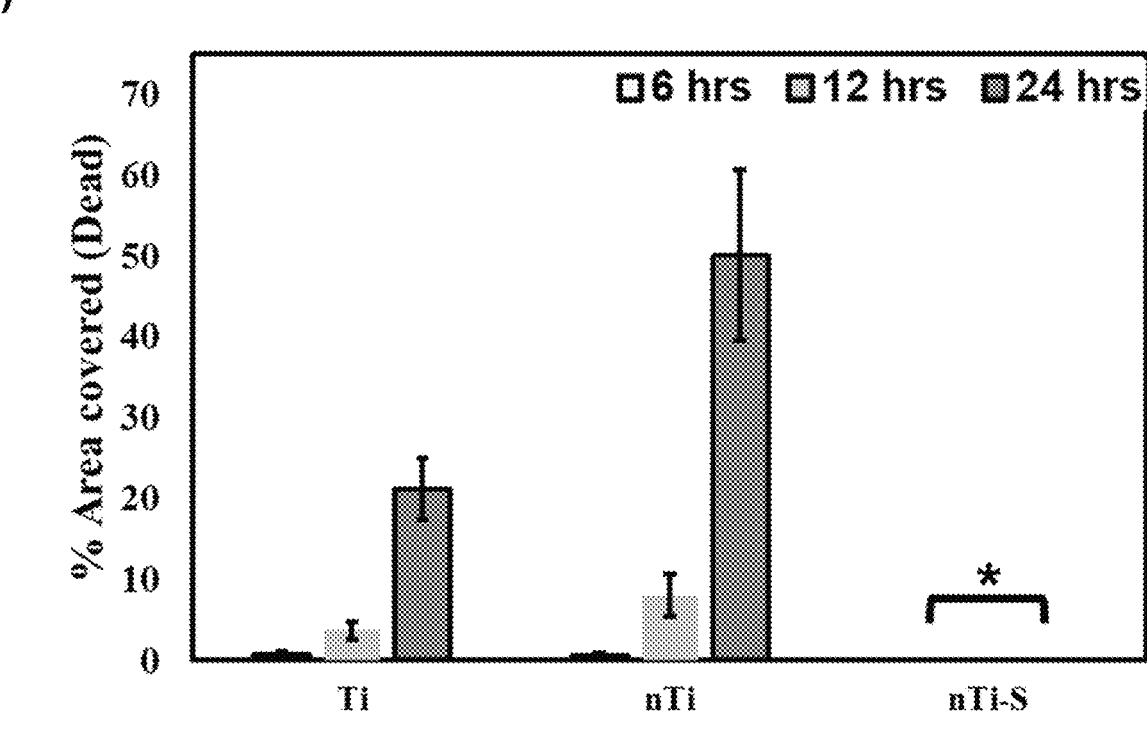

FIG. 9. a) Fluorescence images of adhered *S. aureus* live and dead bacteria on different surfaces. Insert images depict higher magnification. b) Percentage of the areas covered by the live bacteria cells adhered on different surfaces. c) Percentage of the areas covered by the dead bacteria cells adhered on different surfaces. *p<0.05 indicates statistical significance. The error bar represents the standard deviation. Bacterial adhesion and proliferation studies were performed on at least 9 different substrates of each surface ($n_{min}$=9).

Figure 10:
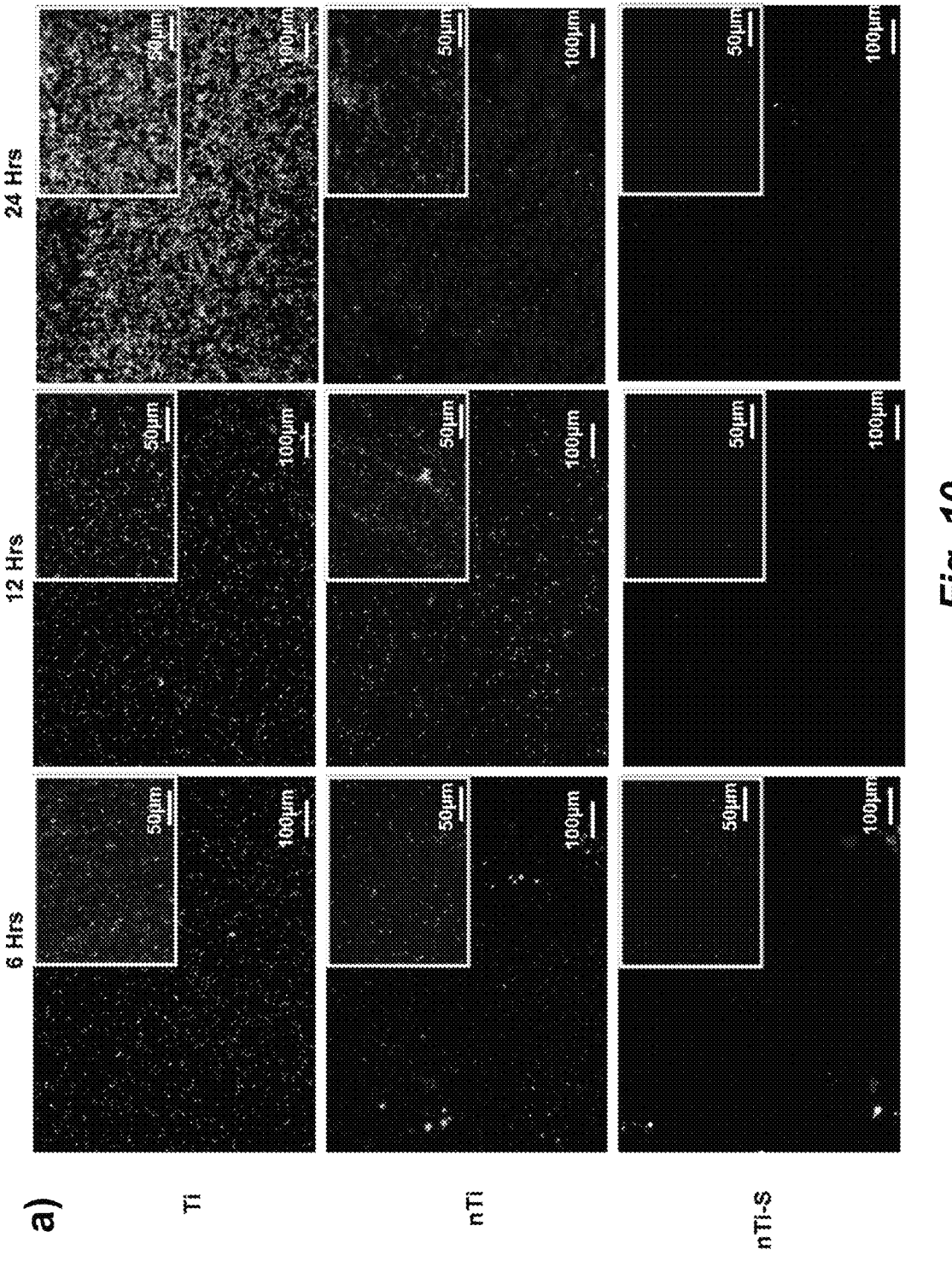
Figure 10:
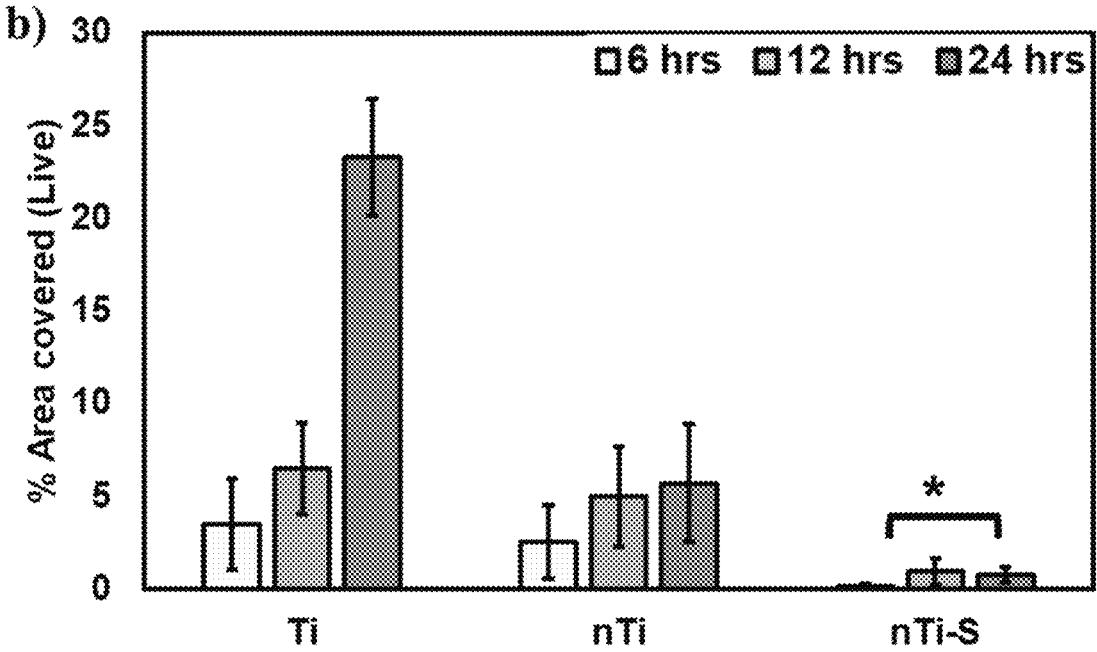
Figure 10:
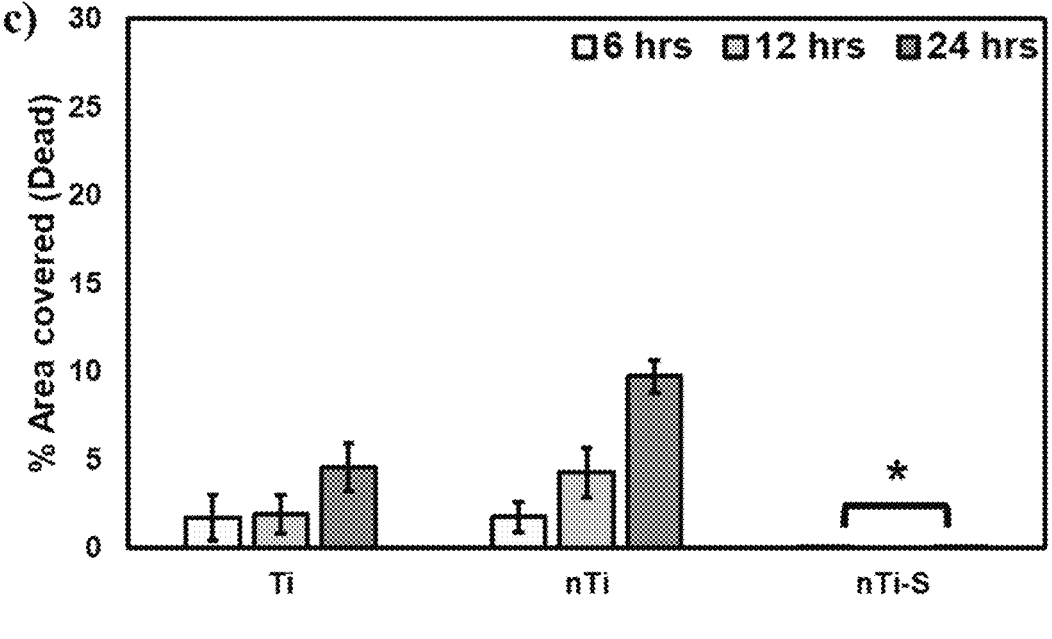

FIG. 10. a) Fluorescence images of adhered *E. coli* live and dead bacteria on different surfaces. Insert images depict higher magnification. b) Percentage of surface area covered by live bacteria cells adhered on different surfaces. c) Percentage of surface area covered by dead bacteria cells adhered on different surfaces. *p<0.05 indicates statistical significance. The error bar represents the standard deviation. Bacterial adhesion and proliferation studies were performed on at least 9 different substrates of each surface (n min=9).

Figure 11:
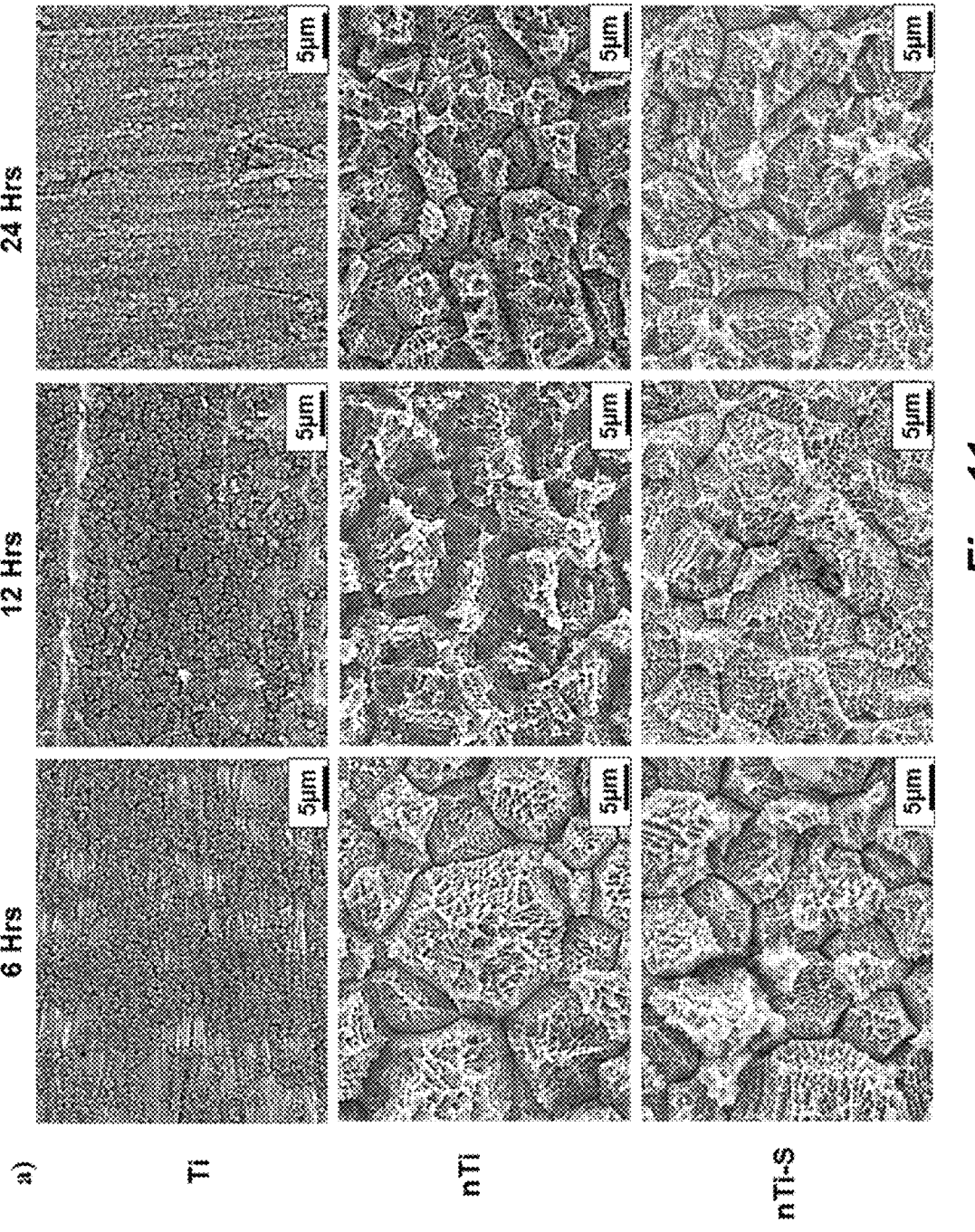
Figure 11:
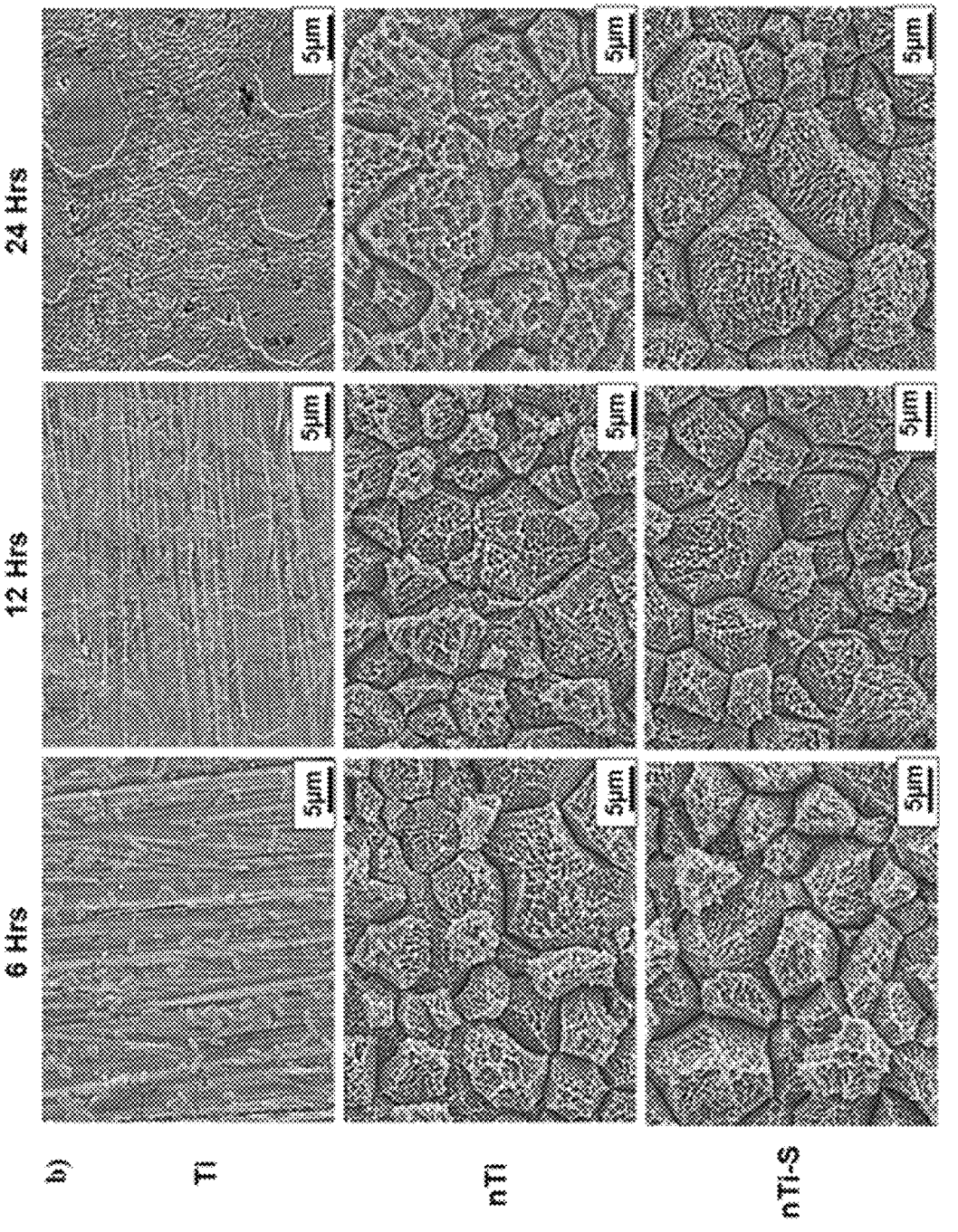

FIG. 11. a) SEM observation of *S. aureus* bacteria cell interaction with the surface topography and biofilm formation. Images were taken at 2000× magnification. The bacteria cells are colored. b) SEM observation of *E. coli* bacteria cell interaction with the surface topography and biofilm formation. Images were taken at 2000× magnification. The bacteria cells are colored. Bacterial adhesion morphology studies were performed on at least 9 different substrates of each surface ($n_{min}$=9).

Figure 12:
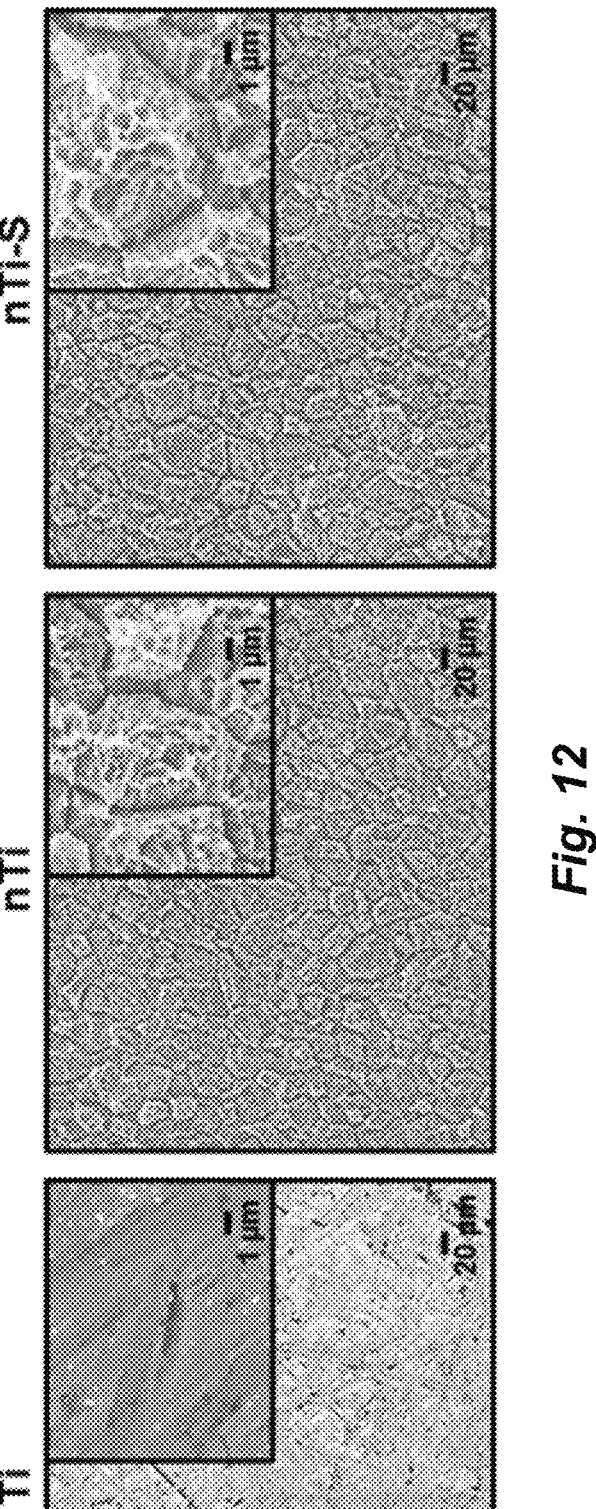
Figure 12:
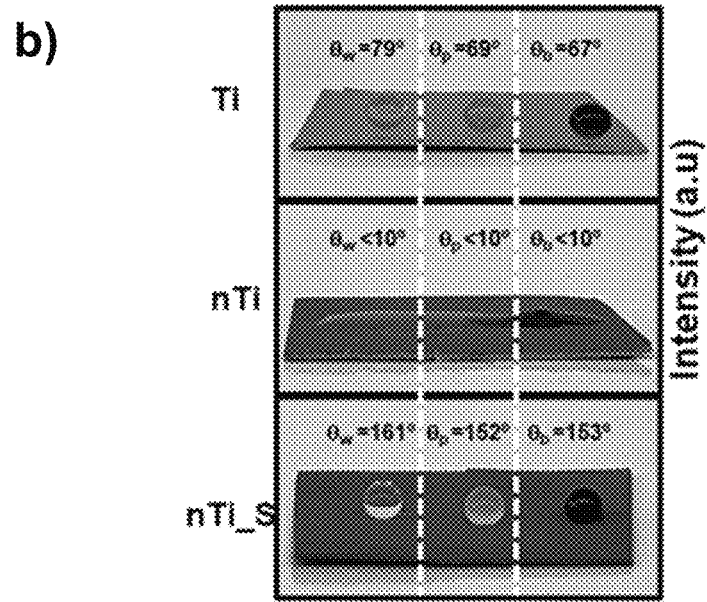
Figure 12:
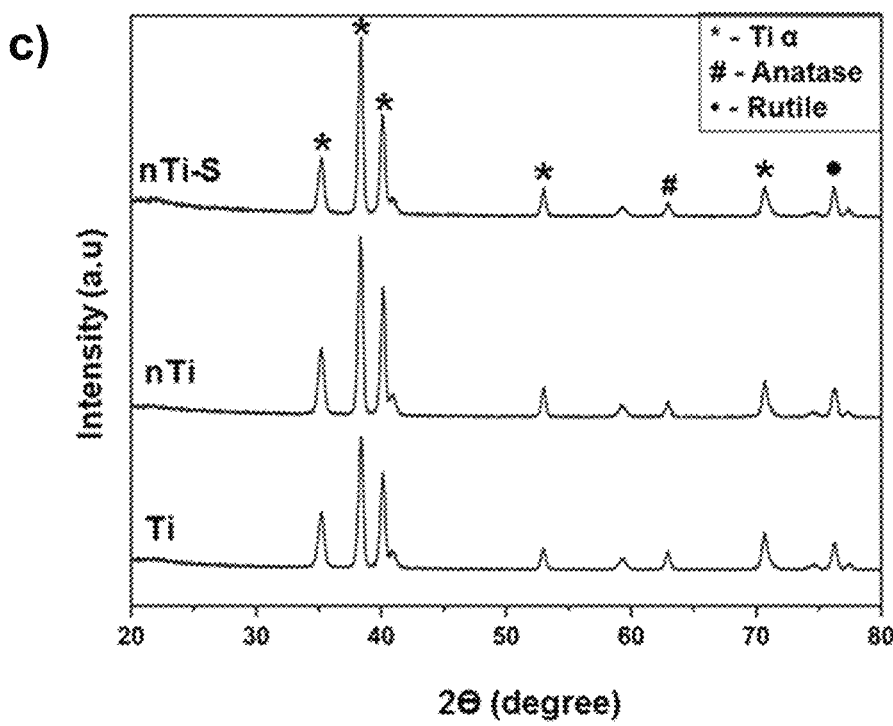

FIG. 12. a) Representative SEM images of different titanium surfaces. Images were taken at 500×; image inserts depict 5000× magnification. b) Apparent contact angle measurements using Milli-Q water, platelet rich plasma, and blood, on different surfaces. c) XRD peak scan of different surfaces. XRD scans were collected at θ=1.5° and 2θ ranges were chosen based on significant peak intensities. Detector scans were run at a step size of 0.01 with a time/step of 1 s.

Figure 13:
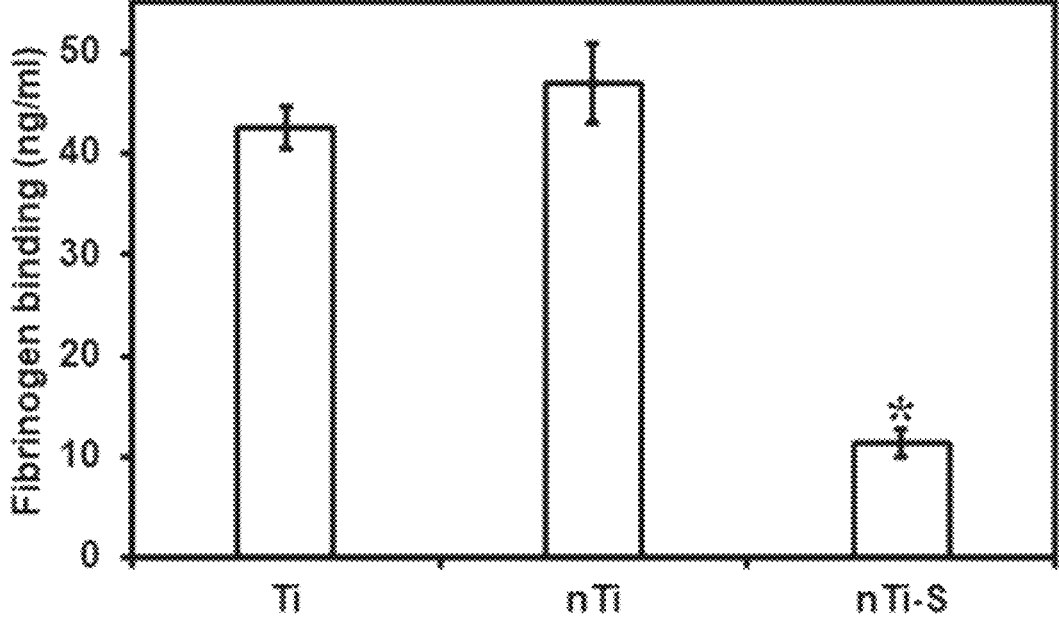

FIG. 13. Fibrinogen binding from PRP on different surfaces measured using spectrophotometer. The results indicate a significant reduction in fibrinogen binding on superhydrophobic micro-nanoporous surfaces (nTi-S) when compared to all surfaces (*p<0.05). The error bar represents the standard deviation.

Figure 14:
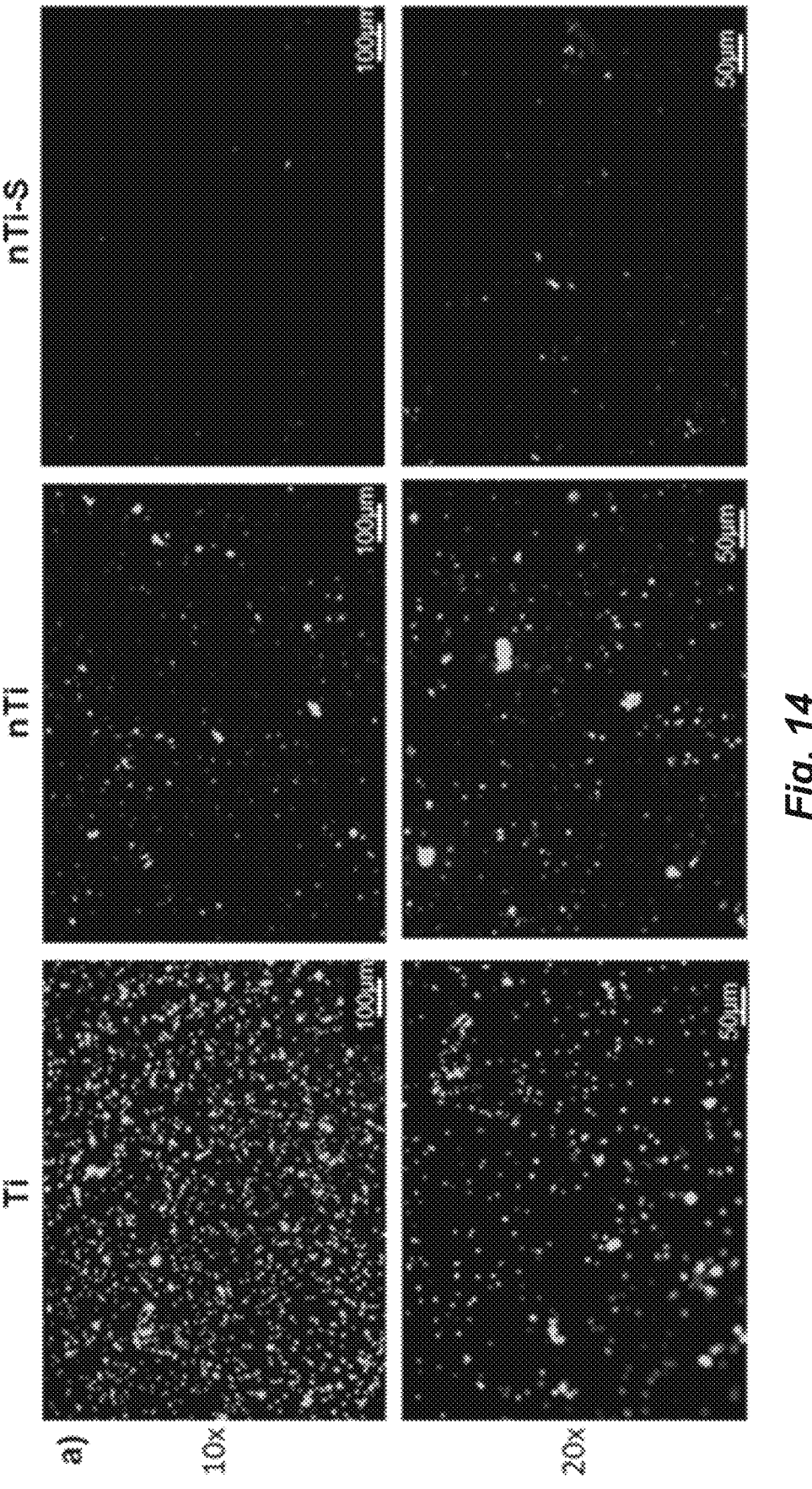
Figure 14:
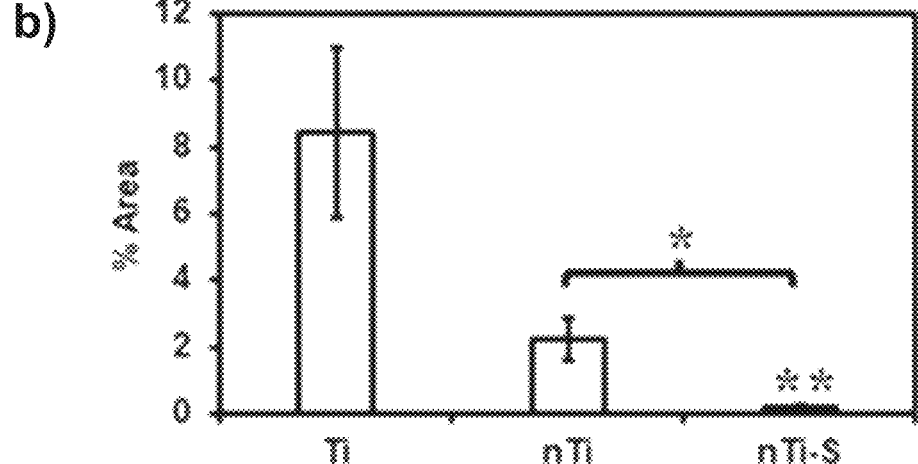
Figure 14:
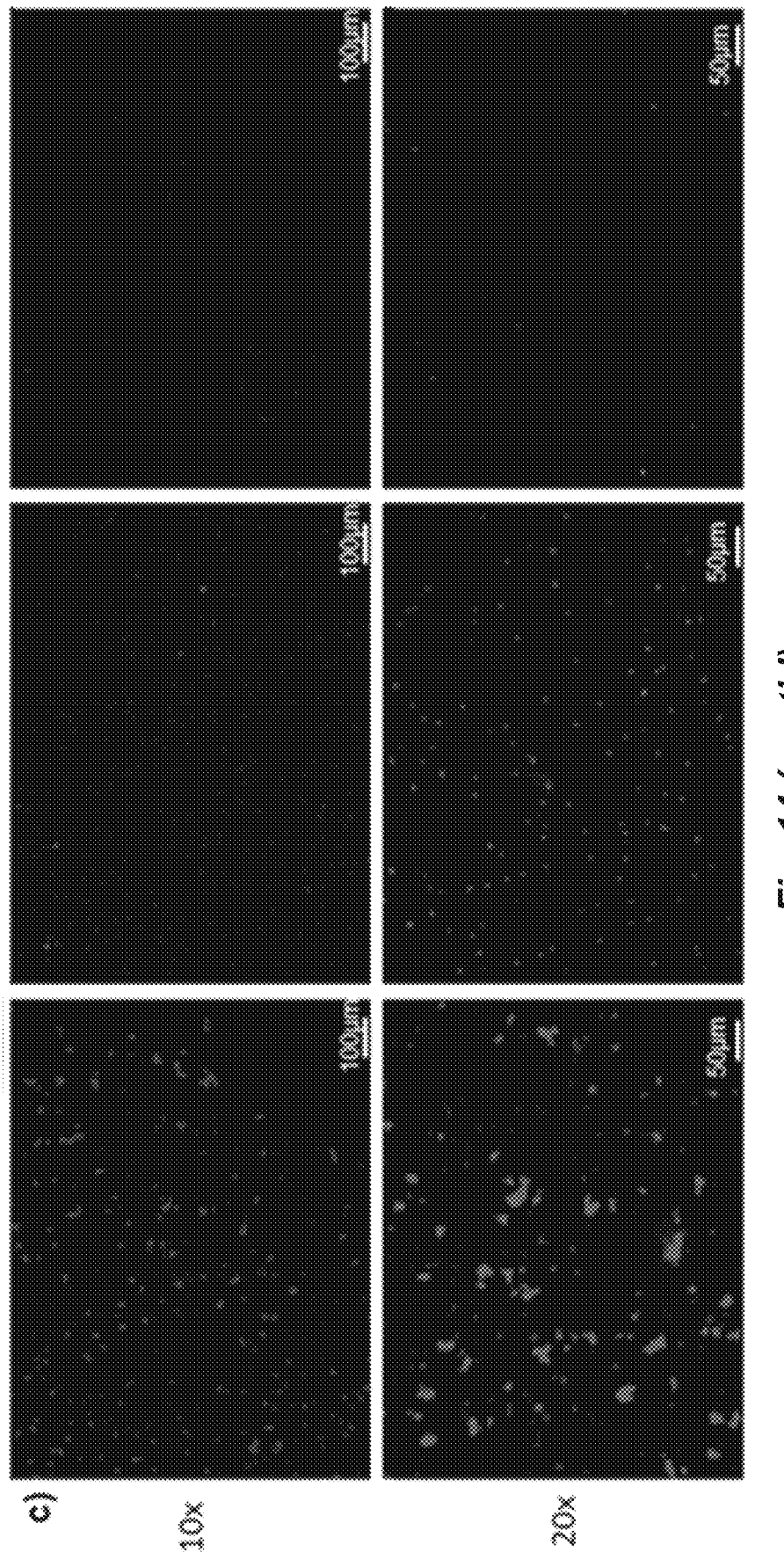
Figure 14:
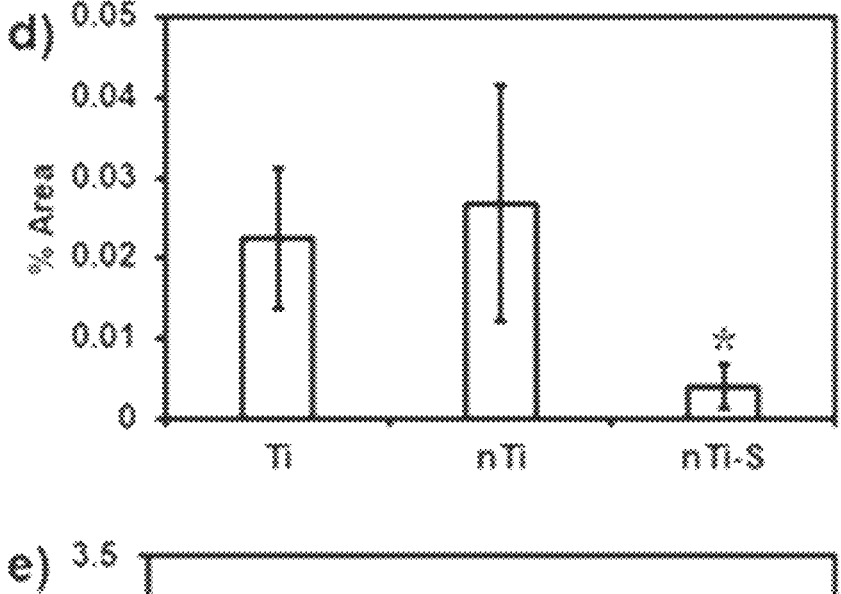
Figure 14:
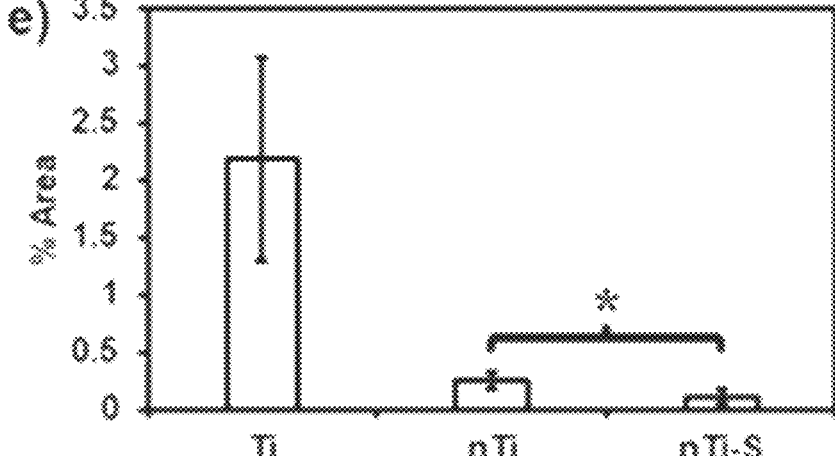

FIG. 14. a) Fluorescence images of adhered platelets and leukocytes on different surfaces. b) Percentage area covered by adhered platelets and leukocytes on different surfaces. c) Fluorescence images of adhered platelets and leukocytes on different surfaces. d) Percentage of area covered by adhered platelets on different surfaces. e) Percentage of area covered by adhered leukocytes on different surfaces. The results indicate significantly lower platelets and leukocytes adhesion on nTi-S when compared to all surfaces (*p<0.05, **p<0.005). The error bar represents the standard deviation.

Figure 15:
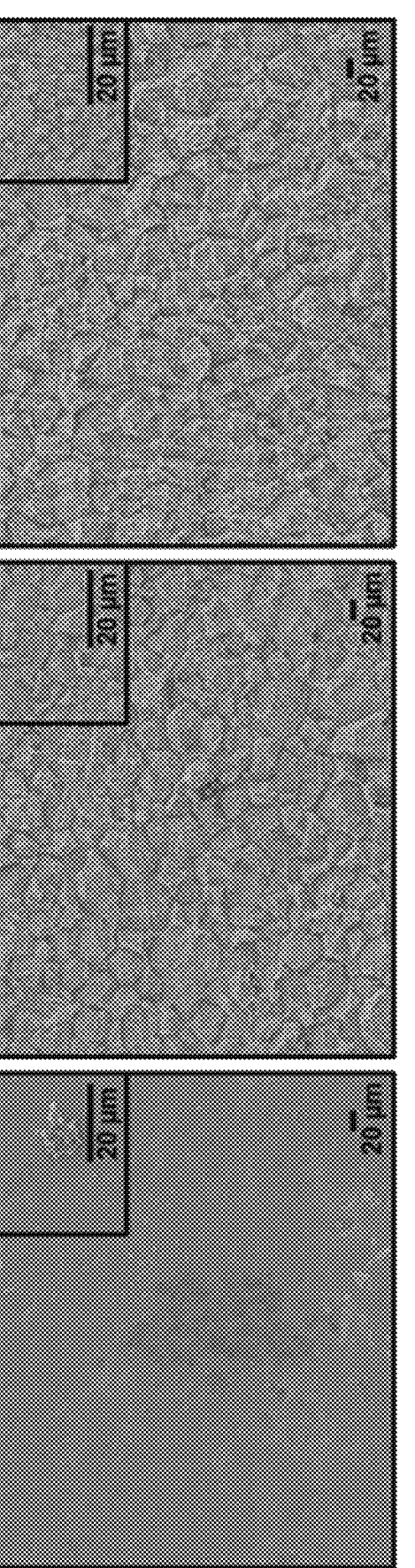

FIG. 15. Representative SEM images of adhered platelets and leukocytes on different surfaces. Images were taken at 500×, and image inserts depict 2000× magnification.

Figure 16:
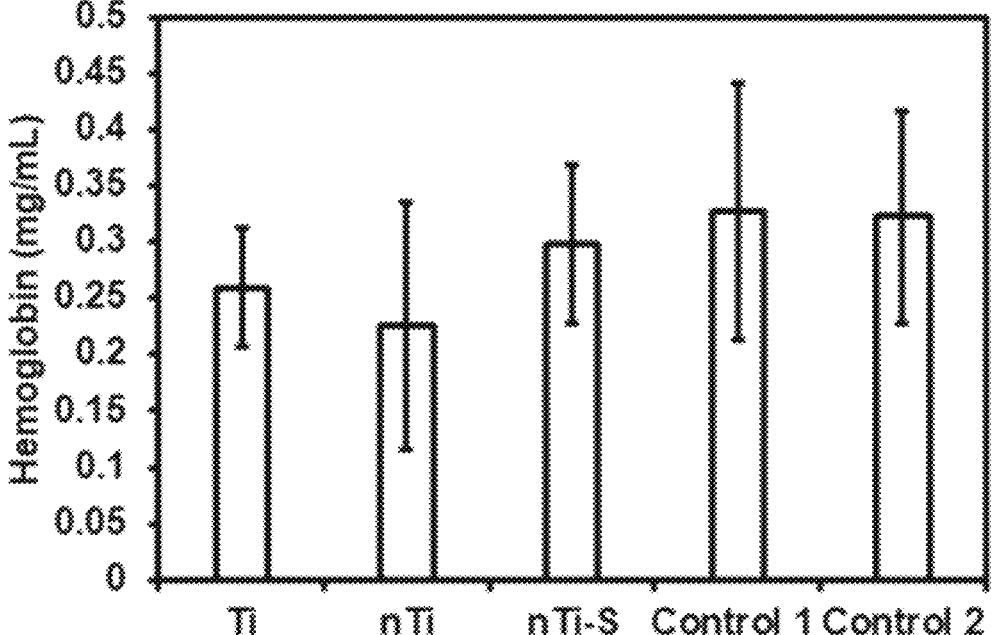

FIG. 16. Hemoglobin release from an erythrocyte suspension incubated with different surfaces was measured with a spectrophotometer. The results indicate no significant difference between all surfaces. The error bar represents the standard deviation.

Figure 17:
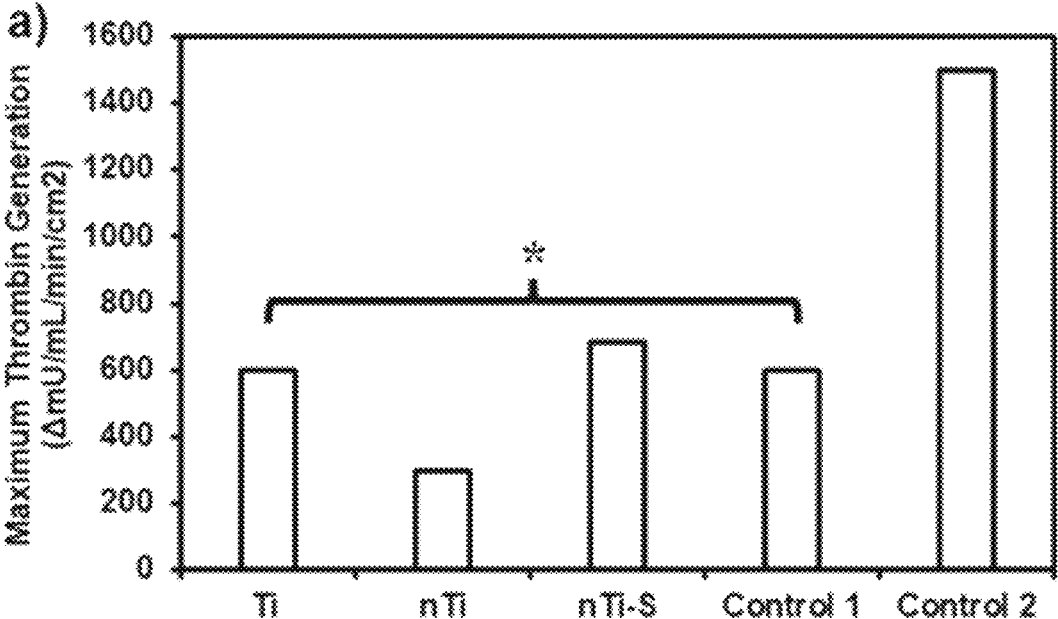
Figure 17:
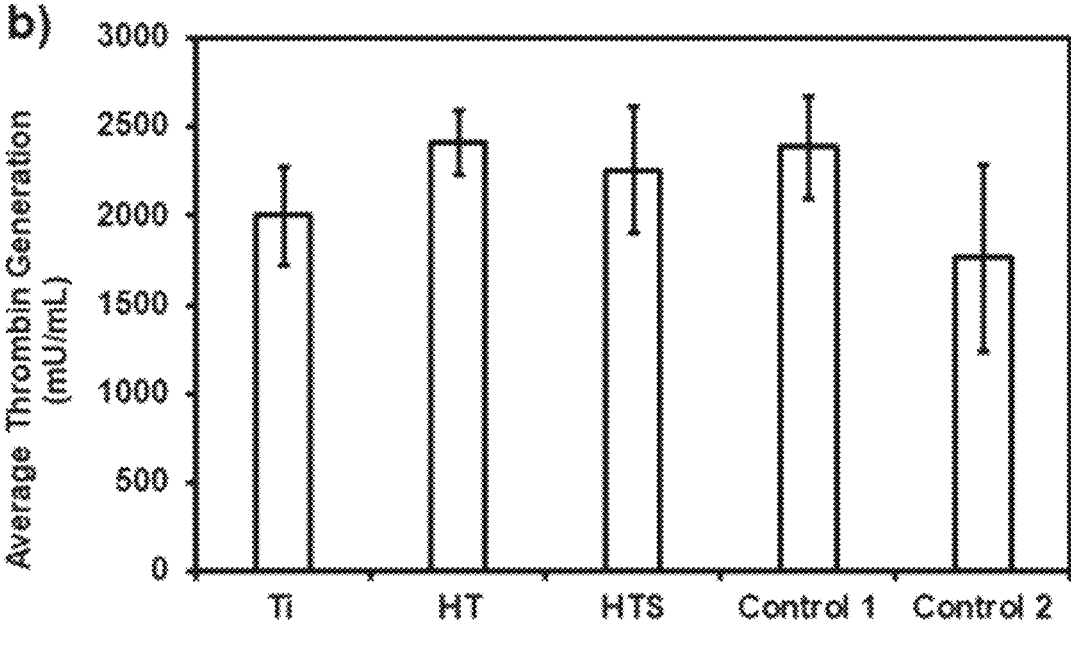

FIG. 17. a) Highest thrombin generation velocity of plasma incubated with different surfaces between two points. b) Average thrombin generation was measured using a spectrophotometer. The results indicate no significant difference between all surfaces. The error bar represents the standard deviation.

Figure 18:
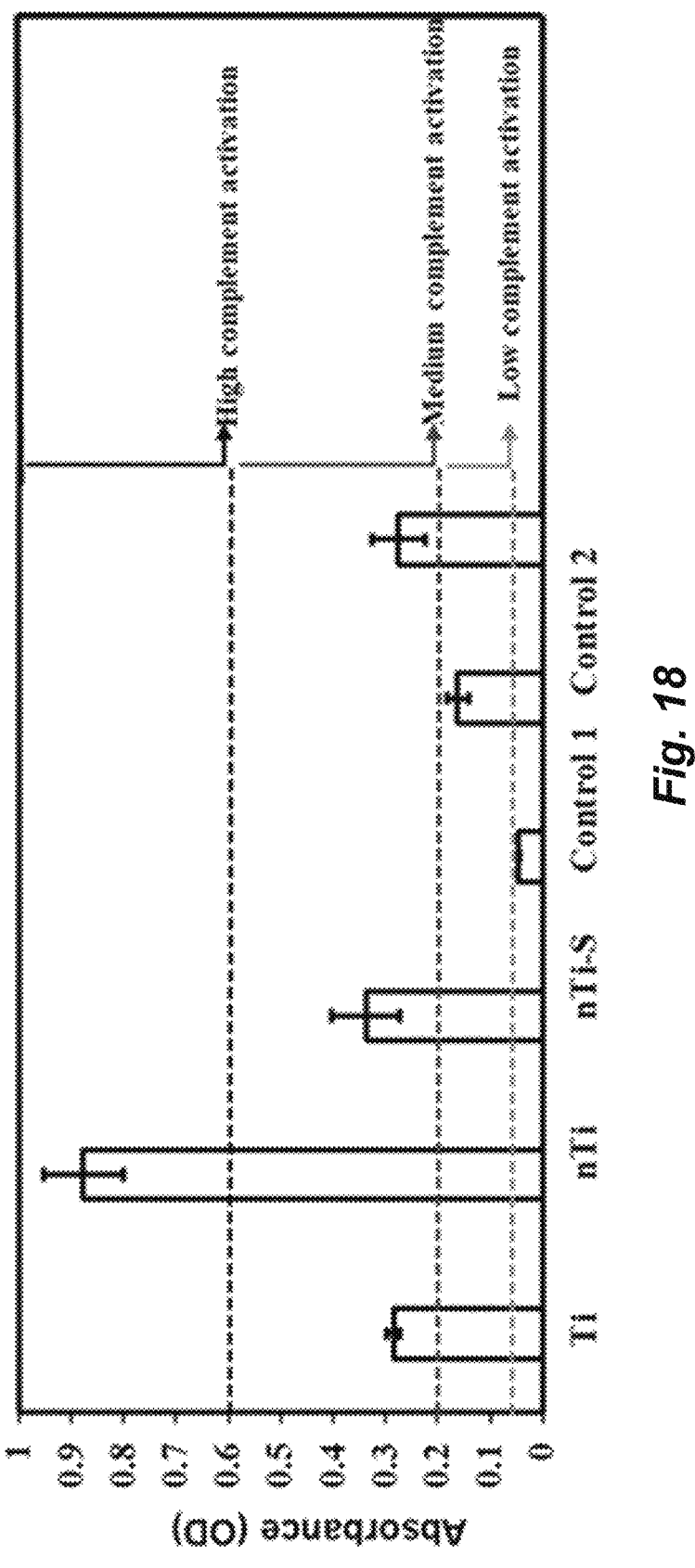

FIG. 18. Complement activation of plasma incubated with different surfaces was measured as activation of complement convertase C5a. The dotted lines indicate cut-offs for inactive/low (≤0.2), medium (>0.2 and ≤0.6), and high (>0.6) reactivity classified according to assay protocols. The results indicate nTi has high complement C5a activation. The error bar represents the standard deviation.

Figure 19:
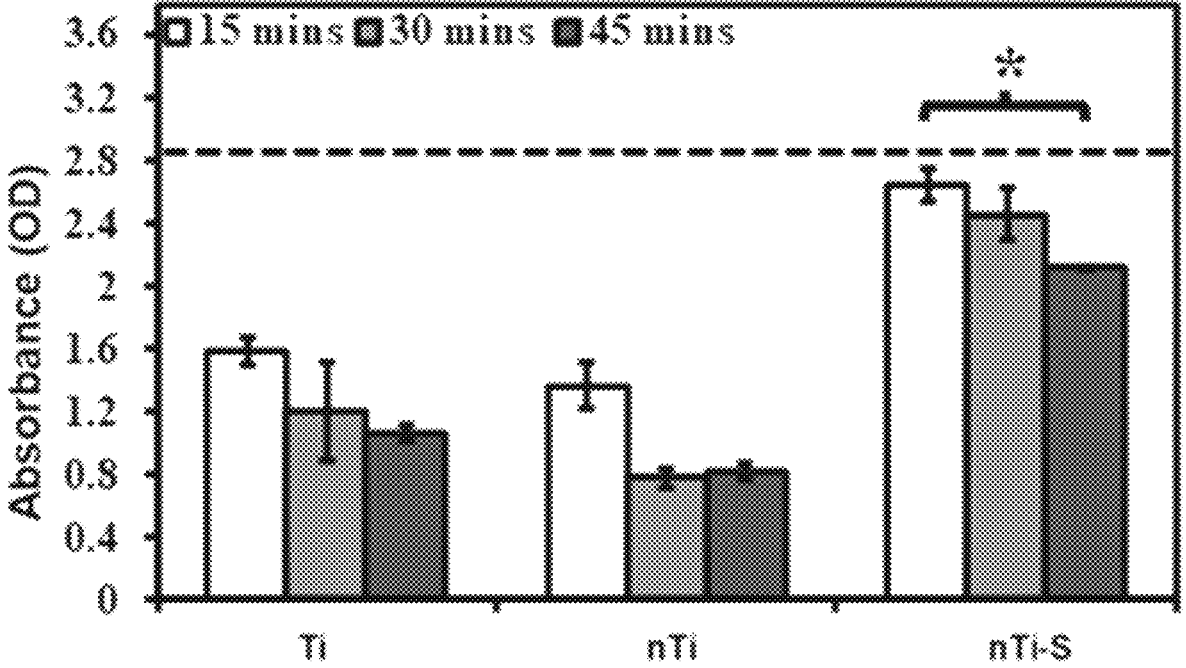

FIG. 19. Whole blood clotting on different surfaces for up to 45 minutes. The dashed line represents the absorbance of free hemoglobin in un-clotted blood. The results indicate significantly lower blood clotting on nTi-S when compared to all surfaces (*p<0.05). The error bar represents the standard deviation.

Figure 20:
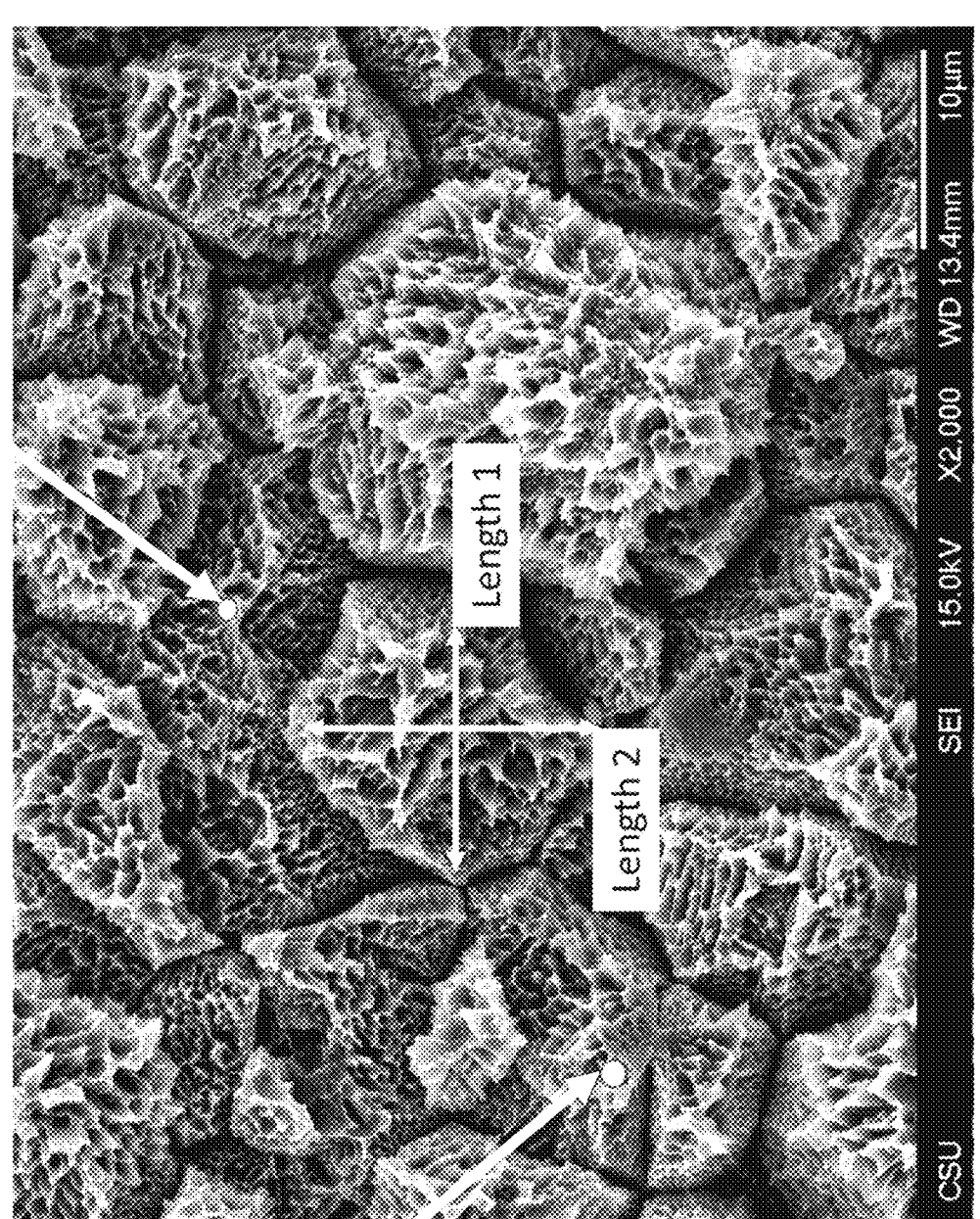

FIG. 20. An SEM image of superhemophobic surface topography showing nanopits (indicated by the circle at the tip of the diameter label) and micrograin structures (with length indicated by the two-headed arrows). Dimensions of various superhemophobic surface features were calculated according to the nanopit diameter and micrograin length as shown in the figure and described in Example 4.

DETAILED DESCRIPTION

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For instance, one or more perfluoroalkyl groups on a silicon atom refers to one to four (e.g., 1, 2, 3, or 4), or one to three, for example if the silicon atom is bonded to a titanium surface.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the endpoints of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

This disclosure provides ranges, limits, and deviations to variables such as volume, mass, percentages, ratios, etc. It is understood by an ordinary person skilled in the art that a range, such as "number1" to "number2", implies a continuous range of numbers that includes the whole numbers and fractional numbers. For example, 1 to 10 means 1, 2, 3, 4, 5, . . . 9, 10. It also means 1.0, 1.1, 1.2. 1.3, . . . , 9.8, 9.9, 10.0, and also means 1.01, 1.02, 1.03, and so on. If the variable disclosed is a number less than "number10", it implies a continuous range that includes whole numbers and fractional numbers less than number10, as discussed above. Similarly, if the variable disclosed is a number greater than "number10", it implies a continuous range that includes whole numbers and fractional numbers greater than number10. These ranges can be modified by the term "about", whose meaning has been described above. Furthermore, the recitation of a), b), c), . . . or i), ii), iii), or the like in a list of components or steps does not confer any particular order, unless explicitly stated.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

As used herein, "subject" or "patient" means an individual having symptoms of, or at risk for, a disease or other malignancy, for example a person in need of an implantable medical device. A patient may be human or non-human and may include, for example, animal strains or species used as "model systems" for research purposes, such a mouse model as described herein. Likewise, a patient may be an adult or a juvenile. Moreover, patient may mean any living organism, preferably a mammal (e.g., a human or non-human) that may benefit from the administration of compositions contemplated herein. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the invention provided herein, the mammal is a human.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

An "effective amount" refers to an amount effective to bring about a recited effect, such as an amount necessary to form products in a reaction mixture. Determination of an effective amount is typically within the capacity of persons skilled in the art, especially in light of the detailed disclosure provided herein. The term "effective amount" is intended to include an amount of a compound or reagent described herein, or an amount of a combination of compounds or reagents described herein, e.g., that is effective to form products in a reaction mixture. Thus, an "effective amount" generally means an amount that provides the desired effect.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

Wherever the term "comprising" is used herein, options are contemplated wherein the terms "consisting of" or "consisting essentially of" are used instead. As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the aspect element. As used herein, "consisting essentially of" does not exclude materials or steps that do not materially affect the basic and novel characteristics of the aspect. In each instance herein any of the terms "comprising", "consisting essentially of" and "consisting of" may be replaced with either of the other two terms. The disclosure illustratively described herein may be suitably practiced in the absence of any element or elements, limitation or limitations which is not specifically disclosed herein.

As used herein, the terms titania and titanium are used interchangeably.

The term "topography" or "surface topography" is the arrangement of natural and artificial physical features of a surface. Surface topography includes the distribution of grains, crevices, pits, peaks, valleys, and generally the roughness or bumps or ridges or irregularities on the surface of a sample. A smooth topography refers to a surface free from roughness or bumps or ridges or irregularities. A rough topography refers to a surface comprising roughness or bumps or ridges or irregularities to varying degrees. The degree of topography roughness is dependent on the size (e.g., height and inter-feature distance) of the roughness or bumps or ridges or irregularities. Surface topography is seen in almost all engineered materials and can have a great influence on material properties. Surface topography can be determined by various methods. Some methods allow a quantitative analysis of the texture, while others are only qualitative. Among the quantitative techniques, the most widely used is an optical profilometer. Among the qualitative techniques, the most widely used is Scanning Electron Microscopy (SEM).

The term "perfluorosilane" refers to an alkylsilane wherein hydrogen atoms on multiple carbon atoms have been replaced with fluorine. The alkyl chain of a perfluorosilane typically has 3-18 carbon atoms wherein the majority or all carbon atoms other than C1, or C1 and C2, of the alkyl chain are fluorinated with at least one fluorine substituent. The silicon atom of the perfluorosilane can have 1-3 perfluoroalkyl chains but typically has 1 or 2 perfluoroalkyl chains, with the remaining valencies comprising a halo group, such as chloro, or a bond to a surface. The perfluorosilane is preferably a low surface tension perfluorosilane, for example, a perfluorosilane having a surface tension of less than 20 mN/m, less than 15 mN/m, or less than 13 mN/m. Examples of suitable perfluorosilanes include $C_6$-$C_{16}$ 1H,1H-perfluoroalkylsilanes and 1H,1H,2H,2H-perfluoroalkylsilanes. In some embodiments, the perfluorosilane is a $C_5$-$C_{16}$ perfluorosilane, a $C_{10}$-$C_{16}$ perfluorosilane, or a $C_8$-$C_{12}$ perfluorosilane. Specific examples of suitable perfluorosilanes include heptadecafluoro-1,1,2,2-tetrahydrodecyl trichlorosilane (also known as 1H,1H,2H,2H-perfluorodecyl trichlorosilane or PFDTS), nonadecafluoro-1,1-dihydrodecyl trichlorosilane, and 1H,1H,2H,2H-perfluorooctyl trichlorosilane (PFOTS), as well as the corresponding compounds having 9, 11, or 12 carbons in the perfluoroalkyl group of the perfluorosilane.

The term "superhydrophobic" refers to surfaces that are repellant to liquids according to the Cassie-Baxter state. In the Cassie-Baxter state, liquids sit upon rough edges on the surface, resulting in air pockets that are bounded between the surface and liquid. Superhydrophobic surfaces display very high contact angles, typically >150° and very low roll off angles (i.e., the minimum angle by which the surface must be tilted relative to the horizontal for the droplet to roll off), typically <10° with water (a liquid with high surface tension). Such superhydrophobic surfaces are repellent to blood and bacterial solutions. The phrase "antiadhesive superhydrophobic surface" refers to the superhydrophobic surfaces described herein that are inherently antiadhesive to cells, such as bacteria and blood cells. The disclosed superhydrophobic surfaces are also hemocompatible, which makes them suitable for use on medical implants.

As used herein, "Ti" refers to an unmodified titanium surface with minimal distinguishable topography other than irregularities from mechanical polishing observable by SEM at 5000× magnification, "nTi" refers to a micro-nanoporous titanium surface, and "nTi-S" refers to a superhydrophobic micro-nanoporous surface. See Example 1. nTi and nT-S surfaces both have micro-nanoporous titanium surfaces. The topography of a micro-nanoporous titanium surface shows nanopits and micrograin structures, for example, as shown in FIG. 20.

Embodiments of the Technology

This disclosure provides a superhydrophobic surface comprising contiguous or continuous micrograins of titania, each micrograin surrounded by a crevice, and each micrograin comprising a topography or topology of nanopits shaped by contiguous or continuous peaks and valleys, wherein the superhydrophobic surface is bonded to a coating of a perfluorosilane. In various embodiments, the micrograins are micro scale polygons and/or are immobilized on the superhydrophobic surface. The nanopits and/or crevices can hold pockets of a gas such as air.

The superhydrophobic surface comprises nanopits and micrograins, for example, as shown in FIG. 20. In some embodiments, the superhydrophobic surface comprises a titanium phase that is predominantly the alpha-phase. In various embodiments, the formed superhydrophobic surface comprises a topography of contiguous nano-pits on micro scale polygons (etched grain structures).

In various embodiments, the length (or diameter) of the micrograins is about 8 μm to about 14 μm. In other embodiments, the average length (or diameter) of the micrograins is about 11 μm±5 μm. In various other embodiments, the diameter of the nanopits is about 550 nm to about 850 nm. In other embodiments, the average diameter of the nanopits is 685 nm±180 nm. The average distance between the center of two adjoining nanopits is typically about 400 nm to about 900 nm.

In various embodiments, diameter and/or depth (in nanometers) of the nanopits is about 100 nm to about 2000 nm, or about 100 nm, about 200 nm, about 300 nm, about 400 nm, about 500 nm, about 600 nm, about 700 nm, about 800 nm, about 900 nm, about 1000 nm, about 1500 nm, about 2000 nm, or a range of between any two of the aforementioned values.

The distance between the centers of two nanopits (in nanometers) is about 50 nm to about 700 nm, or about 50 nm, about 100 nm, about 150 nm, about 200 nm, about 250 nm, about 300 nm, about 350 nm, about 400 nm, about 450 nm, about 500 nm, about 550 nm, about 600 nm, about 650 nm, about 700 nm, or a value in between any two cited values.

In various embodiments, diameter and/or depth (in micrometers) of the micrograins is about 3 μm to about 24 μm, about 1 μm, about 2 μm, about 3 μm, about 4 μm, about 5 μm, about 6 μm, about 7 μm, about 8 μm, about 9 μm, about 10 μm, about 15 μm, about 20 μm, about 25 μm, or a range of between any two of the aforementioned values.

Surfaces can be compared and contrasted by their ratios of surface carbon to other surface elements (such as oxygen or titanium) by area under the curve analysis of XPS survey scans. The oxygen to carbon ratio of the superhydrophobic (nTi-S) surface is about 3:1 to about 1:1, as determined by area under the curve analysis of XPS survey scans. In various embodiments, the superhydrophobic surface has an oxygen to carbon ratio of about 3:1, about 2.9:1, about 2.8:1, about 2.7:1, about 2.6:1, about 2.5:1, about 2.4:1, about 2.3:1, about 2.2:1, about 2.1:1, about 2.0:1, about 1.9:1, about 1.8:1, about 1.7:1, about 1.75:1, or about 1.6:1, or a range between any two of the aforementioned ratios. In additional embodiments, the superhydrophobic surface has an oxygen to carbon ratio of less than 3:1, less than 2.9:1, less than 2.8:1, less than 2.7:1, less than 2.6:1, less than 2.5:1, less than 2.4:1, less than 2.3:1, less than 2.2:1, or less than 2.1:1, and/or an oxygen to carbon ratio of greater than 1.6:1, greater than 1.7:1, greater than 1.75:1, greater than 1.8:1, or greater than 1.9:1.

The titanium to carbon ratio of the superhydrophobic surface is about 0.2:1 to about 1:1, as determined by area under the curve analysis of XPS survey scans. In various embodiments, the superhydrophobic surface has a titanium to carbon ratio of 0.2:1, about 0.3:1, about 0.4:1, about 0.5:1, about 0.6:1, about 0.7:1, about 0.8:1, about 0.9:1, or about 1:1, or a range between any two of the aforementioned ratios. In additional embodiments, the superhydrophobic surface has a titanium to carbon ratio of greater than 0.2:1, greater than 0.3:1, greater than 0.4:1, greater than 0.5:1, or greater than 0.55:1, and/or a titanium to carbon ratio of less than 1:1, less than 0.9:1, less than 0.8:1, less than 0.7:1, or less than 0.65:1.

A large portion of the superhydrophobic surface is coated with a perfluorosilane, which is chemically bonded to the surface. This partial coating typically covers about 90% to about 99% of the superhydrophobic surface. In various embodiments, the partial coating covers 99.9%, 99.8%, 99.7%, 99.6%, 99.5%, 99.4%, 99.3%, 99.2%, 99.1%, 99.0%, 98%, 97%, 96%, 95%, 94%, 93%, 92%, 91%, or 90% of the superhydrophobic surface. In some embodiments, the bottom of the nanopits or valleys are uncoated, or substantially uncoated. In further embodiments, the tips of the peaks and valleys are coated or substantially coated.

In certain specific embodiments, the perfluorosilane is a heptadecafluoro-1,1,2,2-tetrahydrodecyl silane or chlorosilane.

In one embodiment, the surface energy of the superhydrophobic surface is less than 5 mJ/M$^2$. In another embodiment, the surface energy is less than 4 mJ/M$^2$. In yet another embodiment, the surface energy is less than 3 mJ/M$^2$. In a further embodiment, the surface energy is about 2 to about 3 mJ/M$^2$, or about 2.25 3 mJ/M$^2$.

In one embodiment, the advancing contact angle ($\theta_{adv}$) with respect to deionized water is greater than 160 degrees. In another embodiment, the advancing contact angle ($\theta_{adv}$) with respect to deionized water is greater than 165 degrees. In yet another embodiment, the advancing contact angle ($\theta_{adv}$) with respect to deionized water is about 160 degrees to about 170 degrees.

The superhydrophobic surface is antiadhesive and hemocompatible. The superhydrophobic surface repels bacteria and can be fabricated for use on a medical device, such as a biomedical implant. In various embodiments, the implant is a cardiovascular implant or an orthopedic implant. For example, the implant can be a heart valve, an endovascular stent, or a neurovascular flow diverter.

The antiadhesive superhydrophobic surface specifically reduces fibrinogen adhesion, platelet adhesion, and leukocyte adhesion, compared to a similar implant lacking the superhydrophobic surface. In various embodiments, the reduction is at least 90%, for example, compared to a similar but unmodified pure titanium surface.

This disclosure also provides a method for fabricating an antiadhesive superhydrophobic surface, such as the surface described above. The method comprises:

a) contacting a titanium surface and sulfuric acid under heating to form a hydrothermally treated surface;

b) annealing the hydrothermally treated surface;

c) etching the annealed surface with oxygen plasma; and d) fluorinating the etched surface with a perfluorosilane to form an antiadhesive superhydrophobic surface.

Prior to step a), the titanium surface can optionally be polished with silicon carbide. The titanium surface is preferably Medical Grate 2 titanium. Use of a titanium-metal alloy surface does not provide a superhydrophobic surface with the properties and robustness of the superhydrophobic surfaces described herein. The prepared superhydrophobic surface can optionally be cleaned (e.g., treated by sonication in a solvent such as acetone) after one or more of steps a) to d).

Use of acids other than sulfuric acid, such as nitric acid, hydrochloric acid, and phosphoric acid, failed to provide a surface with suitable etching required for preparation of a superhydrophobic surface with the properties and robustness of the superhydrophobic surfaces described herein.

The heating of step a) is generally carried out at an air temperature of about 30° C. to about 500° C., or about 50° C. to about 150° C. In some embodiments, the heating is carried out at a temperature of about 70° C., about 80° C., about 90° C., about 110° C., about 130° C., about 250° C., about 330° C., or about 500° C.

The sulfuric acid used in step a) can be concentrated sulfuric acid, or it can be aqueous sulfuric acid, for example, having a concentration of about 0.1% to about 99%, often about 5%-50%, and in some embodiments, about 5%, about 10%, about 20%, about 30%, or about 40%. In various embodiments, the concentration of the sulfuric acid can be about 0.1M to about 2M, for example, about 0.1M, about 0.5M, about 1M, or about 1.5M.

The annealing is typically carried out at a temperature of about 50° C. to about 500° C., about 50° C. to about 400° C., about 200° C. to about 500° C., about 200° C. to about 400° C., about 400° C. to about 500° C., or about 200° C. to about 400° C. In some embodiments, the annealing temperature is about 250° C., about 300° C., or about 350° C.; optionally +/−25° C. or +/−50° C.

The etching typically comprises an oxygen gas flow of about 1 $cm^3$/min to about 30 $cm^3$/min for the oxygen plasma. In various embodiments, the gas flow is about 5 $cm^3$/min, about 10 $cm^3$/min, about 15 $cm^3$/min, about 20 $cm^3$/min, or about 25 $cm^3$/min.

The fluorinating can be performed by any suitable and effective method but is typically performed by vapor deposition. In one specific embodiment, the perfluorosilane is heptadecafluoro-1,1,2,2-tetrahydrodecyl trichlorosilane. The fluorinating is generally performed at a temperature of about 100° C. to about 150° C. In some embodiments, the temperature is about 110° C., about 120° C., about 130° C., or about 140° C.

Implant-Associated Infections and Thrombosis.

Biomedical implants are prone to cause blood clotting and infections. Infections associated with implants often develop bacterial biofilms and are therefore difficult to treat. Bacterial biofilm is a complex three-dimensional extracellular polymeric substance that holds a cluster of bacteria together. The biofilm acts as a protective layer against effects of antibiotics, immune responses, nutrient deprivation, and pH changes. In infected patients, bacterial cells at the periphery of the biofilm can detach and spread the infection further to other parts of the body. The tissue response for the bacteria biofilm also leads to inflammation, formation of granulation tissue, and fibrous encapsulation of biomedical implants. When a bacterial biofilm develops on an implant post-surgery, revision implant surgery is typically required.

Biofilm phenotype bacteria cause 65 to 80% of all human infectious diseases and 99% of biofilm forming bacteria are gram-positive *Staphylococcus* species (*S. aureus* and *S. epidermis*) and 15% of implant infections are gram-negative bacilli species (*E. coli* and *P. aeruginosa*). Unfortunately, an overuse of antibiotics has resulted in the development of several antibiotic strains of bacteria, including a *Staphylococcus aureus* variant that is resistant to methicillin, and an *Enterococcus* variant resistant to vancomycin. Some bacteria have also developed tolerance toward ethanol-based disinfectants, making it difficult to completely eradicate them in clinical settings. As a result, there has been in increase in the occurrence of implant infections from surgical procedures.

Environmental conditions such as pH, temperature, bacteria type (gram-positive/gram-negative), and bacteria shape and size, also influence infection rates. While these factors are not controllable, implant properties such as surface topography (roughness, porosity, etc.) and physio-chemical properties (wettability, chemistry, charge, etc.) can influence bacteria adhesion and biofilm formation on an implant surface so researchers have attempted to modulate implant properties by various techniques to make antibacterial implant surfaces.

Implant surfaces doped with varying amounts of bactericidal materials such as silver, copper, and zinc have been investigated. The major limitation of these approaches is that their metal ions can diffuse into the surrounding tissues over time, causing toxicity and necrosis. Photocatalytic materials have been shown to have antibacterial properties when exposed to UV light. However, these materials have also shown poor long-term stability.

In recent years, there has been an increased demand for cardiovascular implants to repair and replace damaged tissues. Titanium has been used for several cardiovascular implants such as endovascular stents, neurovascular flow diverters, structural heart devices and heart valve casing. Titanium and its alloys have been a preferred choice of material for these implants because of excellent mechanical properties, corrosion resistance, and bio/hemo-compatibility. However, these implants can fail due to problematic surface interactions with blood and blood components, leading to initiation of the coagulation cascade followed by thrombus formation and inflammation.

Patients with cardiovascular implants are prescribed systemic (dual) anti-platelet and/or anticoagulant drugs in clinical settings to avoid thrombus formation on the implant surface. However, the overuse of these drugs can lead to internal bleeding, especially in elderly patients and patients already prone to bleeding. In addition, anticoagulant therapy has variable responses due to genetic variability and patient compliance.

Thrombus formation on an implant surface is due to the hemodynamic alteration of blood flow and improper interactions by the implant compared to the native endothelial layer covered arteries. When blood contacts an implant surface, plasma proteins such as fibrinogen and von Willebrand factor adsorb onto the surface. These proteins alleviate coagulation cascade and thrombin formation. Fibrinogen adsorption further promotes platelet and leukocyte adhesion and activation. Simultaneously, there is contact activation of intrinsic coagulation pathway by adsorbing factor XII and its subsequent change in confrontation and activation. Activated FXIIa initiates activation of other factors, leading to formation of thrombin and complement activation on the surface. Thrombin reacts with fibrinogen and forms mesh to trap activated platelets and red blood cells to form blood clot. Additionally, activation of coagulation cascade is greatly interconnected with platelets and leukocytes adhesion and activation. This understanding of cardiovascular implant surface interactions with blood and its components can aid the development of surfaces that prevent protein adsorption and thrombus formation.

Biomedical implant blood biocompatibility can depend on the implant surface topography, chemistry, crystallinity, and charge. Surface passivation techniques such as plasma treatment, anodization, and hydrothermal treatments can be used to the surface micro/nanoscale topography and chemistry. These modified surfaces are normally hydrophilic and have been shown to influence hemocompatibility. While hydrophilic surface-induced interactions have proven highly advantageous for some implants, surface interaction for blood contacting implants can also increase the risk of thrombus formation. In an attempt to address this problem, biopolymers such as heparin, chitosan, and some zwitterionic polymers have been investigated for preventing protein and platelet attachments. However, these approaches have yet to be approved for any clinical applications and biomedical implant procedures continue to be associated with unacceptable rates of infection and blood clotting. Accordingly, there is a need for implants that reduce patient susceptibility to blood clotting and bacterial infections.

Superhydrophobic Micro-Nano Structured Titanium Surfaces.

A solution to these and related problems associated with biomedical implants discussed above is provided by the superhydrophobic surfaces described herein, which can be used for biomedical implants, including cardiovascular implants. Superhydrophobicity is achieved by a combination of controlling micro- and nano-scale surface topography along with surface chemistry. The right surface chemistry can be achieved by treating an appropriate surface with silanes such as aminopropyltriethoxysilane, 3-acryloxypropyl-trimethoxysilane+bis-1,2-(triethoxysilyl)ethane, or heptadecafluoro-1,1,2,2-tetrahydrodecyl trichlorosilane, which can significantly reduce platelet and leukocyte adhesion to surfaces.

To develop a superhydrophobic surface, a hydrothermal treatment with sulfuric acid was used to develop micro-nano surface topography on a titanium surface. Titanium-based materials are commonly used for cardiac implants due to their favorable biocompatibility and mechanical properties. However, the implant fails mainly due to improper interaction at the surface level. The micro-nano surface was further modified using heptadecafluoro-1,1,2,2-tetrahydrodecyl trichlorosilane and/or poly-ethyleneglycol 2-[methoxy (polyethyleneoxy)propyl]trimethoxysilane to alter the chemistry and wettability of the surface.

The combined micro-nano surface topography and modification with a low energy perfluorosilane coating to form air pockets provided a superhydrophobic surface, which is also hemophobic, as discussed below.

These surfaces were characterized for apparent contact angle, crystallinity, morphology, wettability, chemistry, corrosion resistance, and surface charge, to understand the changes in surface properties. The antibacterial capability was characterized with *S. aureus* and *E. coli* by evaluating the bacteria cell inhibition and adhesion kinetics. Biofilm formation was evaluated on different surfaces with incubation for up to 24 hours. The results showed that the superhydrophobic micro-nano modified surface decreased bacterial adhesion significantly (>90%) and prevented biofilm formation.

The modified surfaces were also characterized for morphology using a Scanning Electron Microscope (SEM). Wettability was characterized with water, platelet rich plasma, and whole blood using a goniometer. Crystallinity was assessed using an X-ray Diffraction (XRD). The hemocompatibility of the superhydrophobic surface was characterized by evaluating fibrinogen adsorption, blood cell adhesion, platelet activation, hemolysis, thrombin generation, complement activation, and whole blood clotting kinetics. The results showed that the superhydrophobic micro-nano modified surface prevented platelet and leukocyte adhesion significantly (>90%) and prevented thrombus formation.

The novel surface modification can thus provide an implant surface, such as a cardiovascular implant surface, with enhanced hemocompatibility.

Superhydrophobic Surface with Enhanced Antibacterial Properties.

Previous reports have shown that micro/nano scale surface modifications of titanium based orthopedic and cardiovascular implants augment biocompatibility. However, bacterial infection remains a serious concern because they can lead to implant failure, aggravated by increased antibiotic resistance and over usage of antibiotics. Bacteria cell adhesion on an implant surface leads to colonization and biofilm formation, sometimes resulting in morbidity and mortality. Accordingly, there is a need to develop new implant surfaces with antibacterial properties, and properties that prevent protein adhesion and bacteria cell adhesion.

A superhydrophobic surface as described herein was prepared and analyzed. The preparation began with an unmodified titanium surface, referred to herein as "Ti", which was converted by hydrothermal treatment to a micro-nanoporous titanium surface, referred to herein as "nTi", and followed by treatment with a perfluorosilane to provide the superhydrophobic micro-nanoporous surface, referred to herein as "nTi-S". These three surfaces, the Ti, nTi, and nTi-S surfaces. are the subject of the surface studies described throughout this disclosure.

Figure 1:
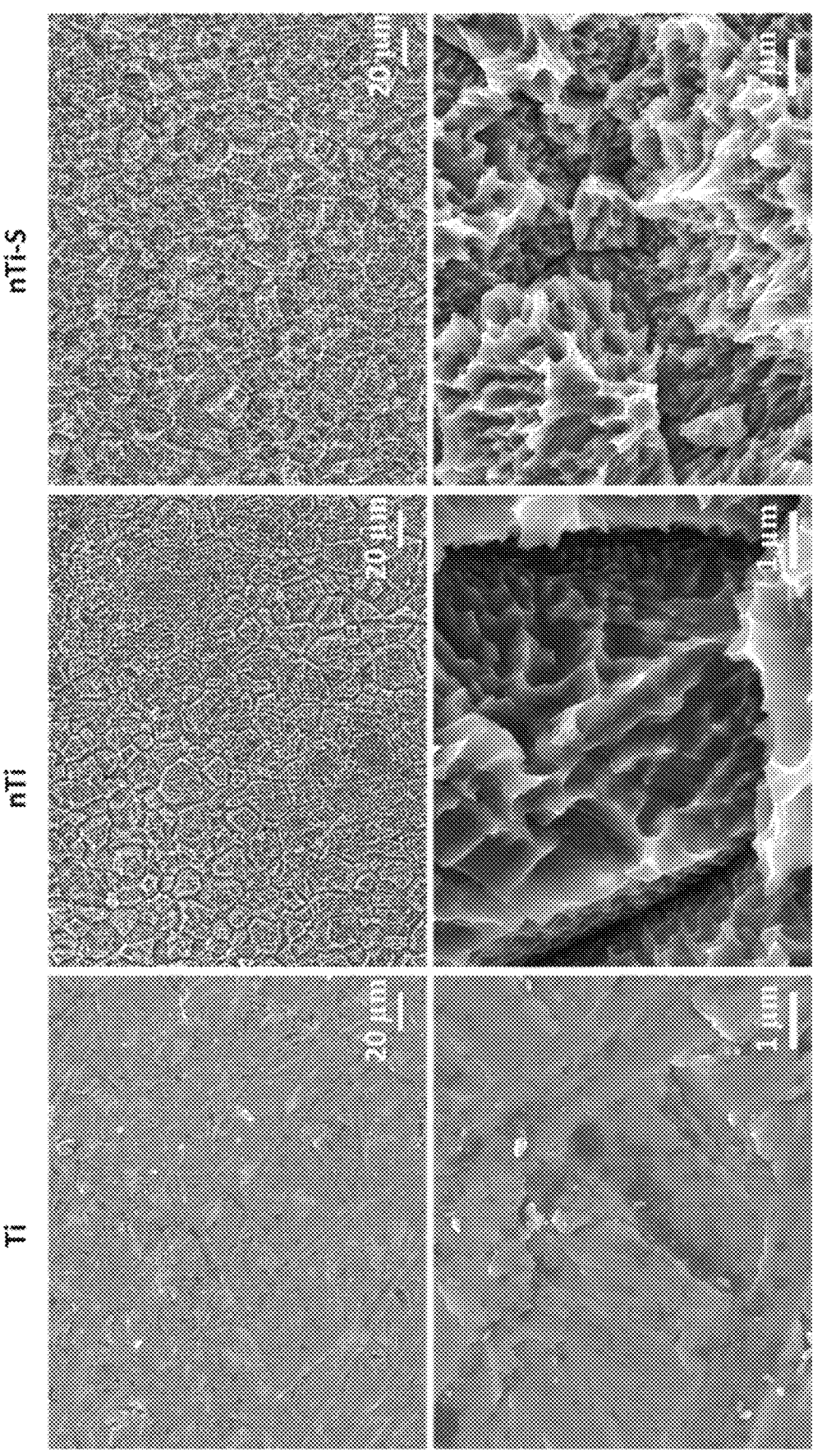
FIG. 1. Representative scanning electron microscopy (SEM) images of different surfaces. Images were taken at two magnifications (500× and 5000×). SEM was carried out on at least 9 different substrates of each surface ($n_{min}$=9).
Figure 2:
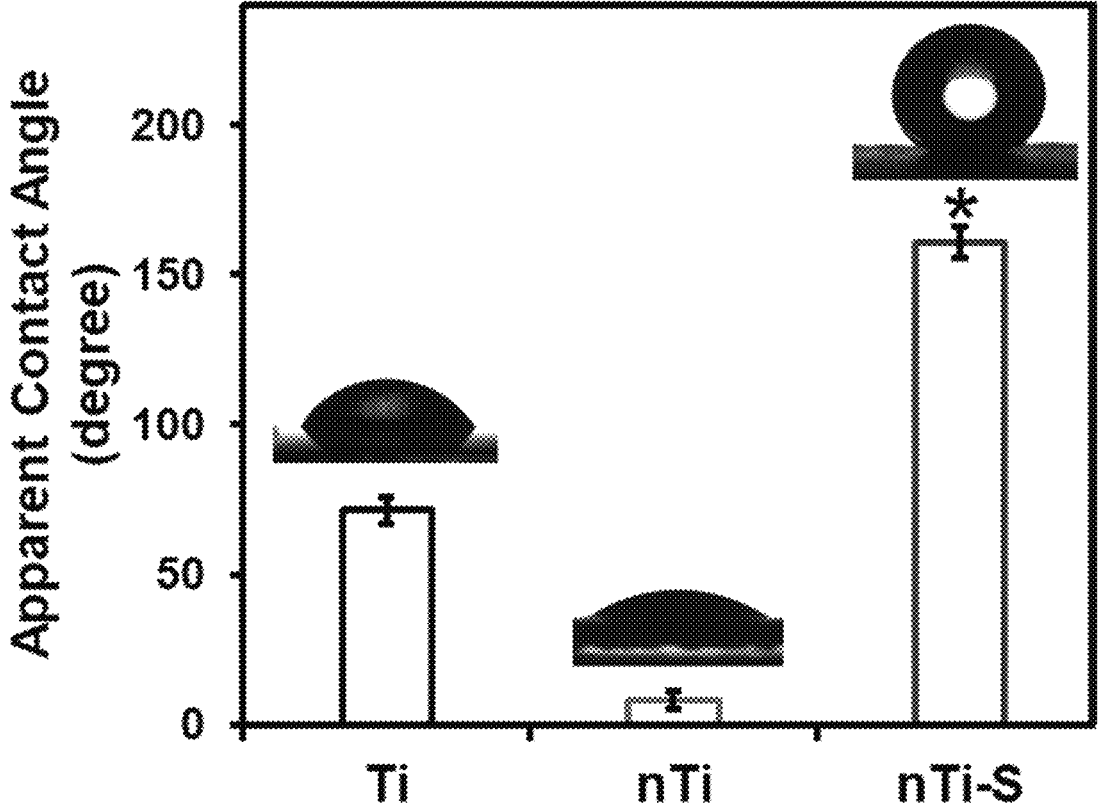
FIG. 2. Apparent contact angle measurements using the sessile drop method for different surfaces. *$p<0.05$ indicates statistical significance. The error bar represents the standard deviation. Contact angle was measured on at least 9 different substrates of each surface ($n_{min}$=9).

Scanning electron microscopy (SEM) was used to analyze the morphology of the three types of surfaces. The results of casual analysis indicated that the Ti surface did not have any distinguishable topography. However, at higher magnification, SEM images show surface irregularities from mechanical polishing by silicon carbide (FIG. 1, left column). After the hydrothermal treatment, the nTi surface developed micro-nano topography (FIG. 1, middle column). The SEM images of the nTi-S surface and the nTi surface showed only minor differences in surface topography (FIG. 1, right column).

A goniometer was used to determine the wettability of different surfaces. Wettability dictates the surface interaction with proteins, cells, and bacteria when implanted into the body. The apparent contact angle ($\theta^*$) is defined as the angle made by the liquid droplet placed on a rough surface. The angle is measured between the liquid-air interface and the solid-liquid interface at the triple phase point passing through the liquid.

A surface is classified as superhydrophilic when $\theta^*$ is less than 10°. Due to hydrothermal treatment, the nTi surface is superhydrophilic, with a $\theta^*$ of ~8°. On the other hand, a surface is classified as superhydrophobic when $\theta^*$ is greater than 150°. In contrast to the nTi surface, the nTi-S surface is superhydrophobic, with a $\theta^*$ of ~160°. As expected, the Ti surface is hydrophilic (~72°) because the surface has no specific topography. The apparent contact angle ($\theta^*$) trend for the three surfaces is therefore nTi-S>Ti>nTi.

The surface energy was characterized to understand and quantify certain surface properties (polar interaction and van der wall forces) and was calculated by measuring the advancing contact angle ($\theta_{adv}$) with DI water (polar) and hexadecane (non-polar), using the Young's and Owens-Wendt equation. See Table 1. The surface energy trend of the three titanium surfaces was nTi>Ti>nTi-S, the reverse of the apparent contact angle ($\theta^*$) trend. The nTi-S surface had significantly low surface energy, indicating that the surface repels most liquids.

TABLE 1

Advancing contact angle and surface energy of different surfaces.

|  | Advancing Contact angle (DI water) | Advancing Contact angle (Hexadecane) | Surface Energy (mJ/M$^2$) |
| --- | --- | --- | --- |
| Ti | 75.74 | 17.7 | 30.66 |
| nTi | 10 | 0 | 71.93 |
| nTi—S | 166.6 | 120.9 | 2.25 |

Figure 3:
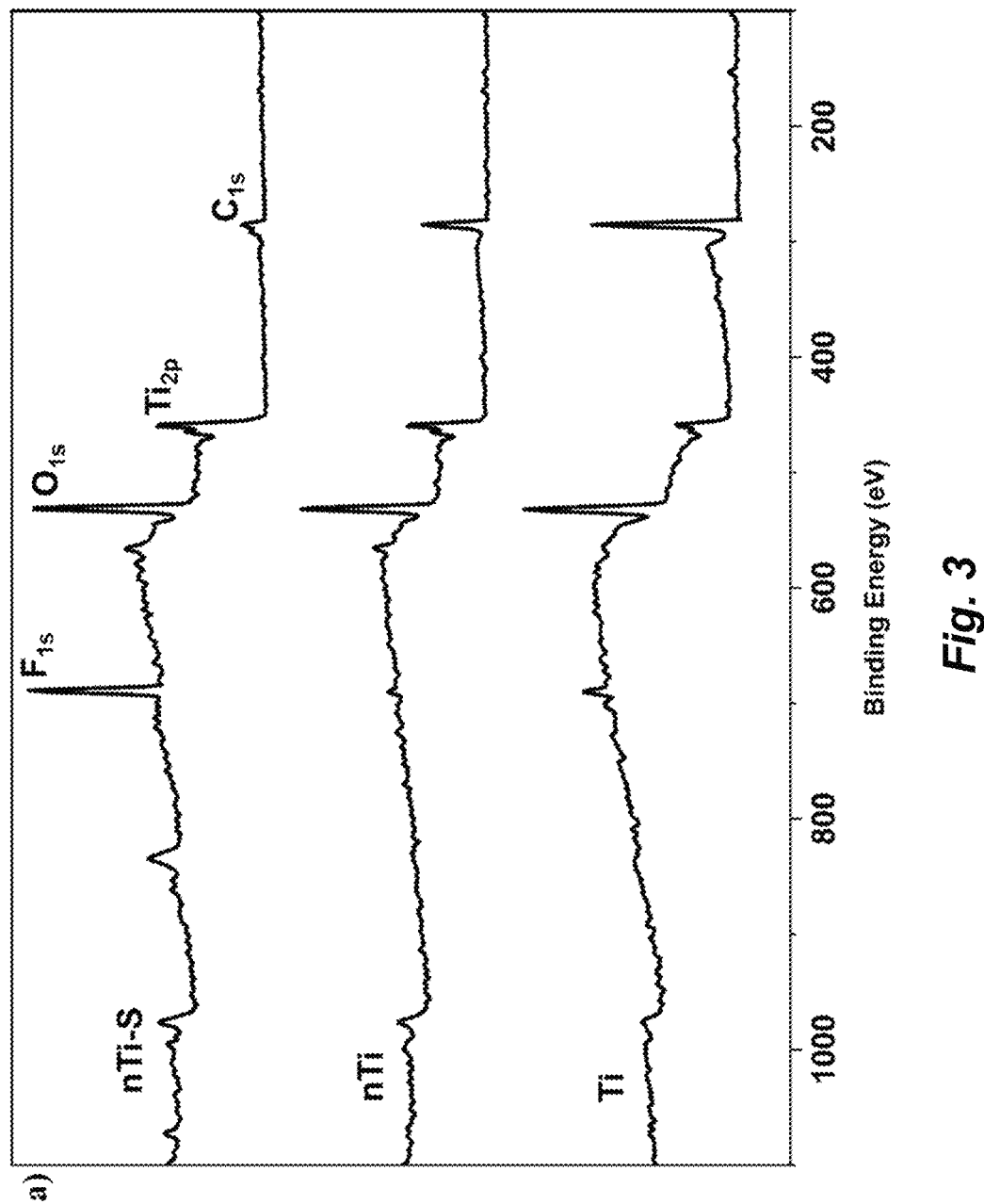
FIG. 3. a) X-ray photoelectron spectroscopy (XPS) survey scans of different surfaces. b,c) High resolution XPS scans
Figure 3:
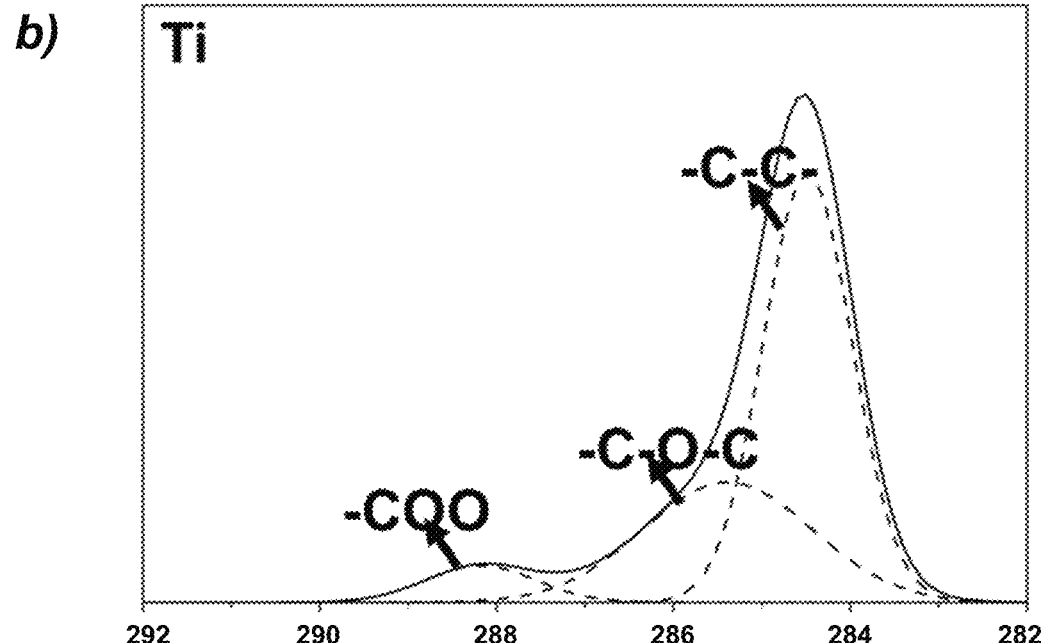
Figure 3:
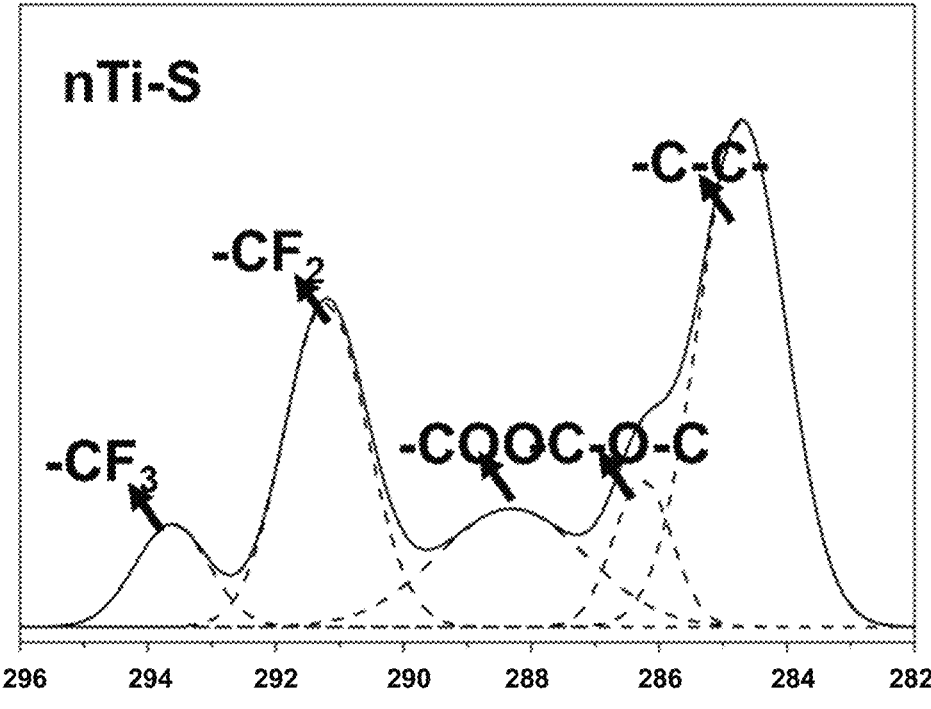
Figure 3:
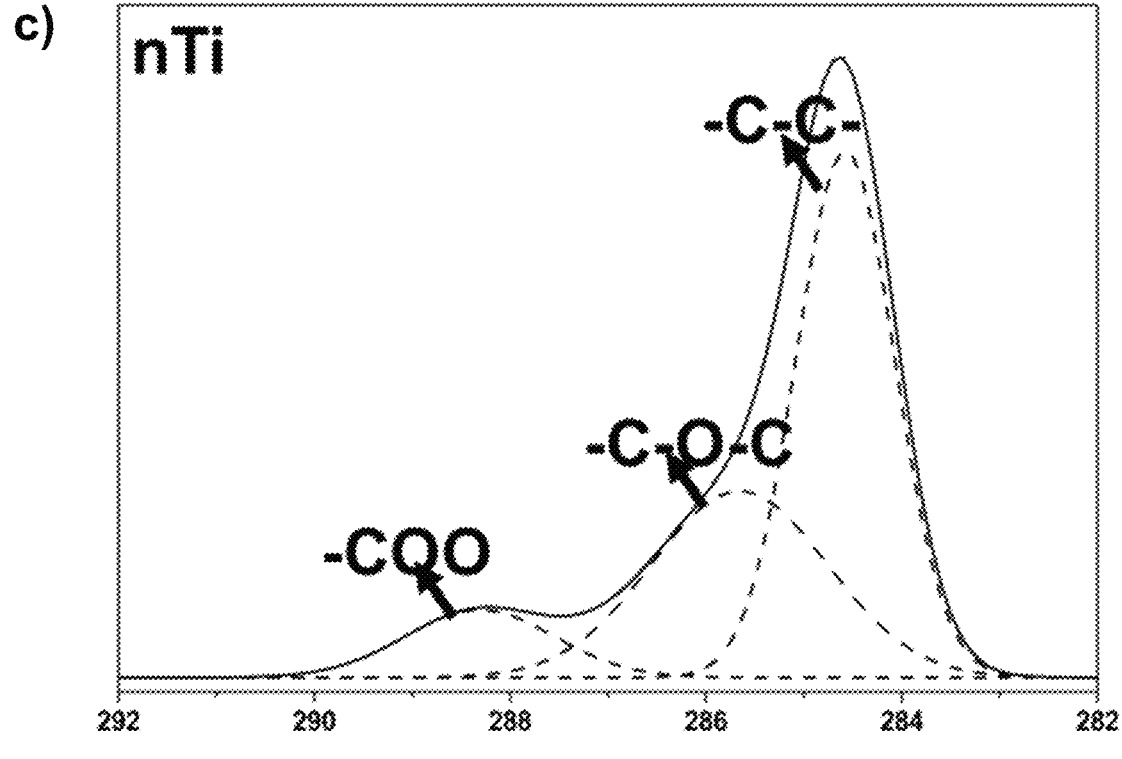

Surface chemistry can dictate the interaction of proteins, cells, and bacteria with the surface, and certain surface elements can induce toxic effects when implanted. The surface chemistry was therefore analyzed by X-ray photo-electron spectroscopy (XPS) to identify elements present on the surfaces. As shown in FIG. 3, the results indicate the presence of C1s (~284.8 eV), O1s (~529 eV), and Ti2p$_{2/3}$ (458.5 eV) peaks on all the surfaces. The C1s content was higher on polished Ti surface (see Table 2) due to presence of impurities on the surface and in the XPS chamber. After hydrothermal treatment, some of the carbon impurities were removed and the native oxide layer was etched, thus increasing the Ti2p$_{2/3}$ peak on the nTi surface. Simultaneously, the exposed Ti2p$_{2/3}$ reacts with the sulfuric acid and water, which results in formation of titania (eq. 1, eq. 2, and eq. 3). Thus, the nTi surface had higher Ti2p$_{2/3}$ and O1s peaks. After modification with silane, the F1s (~689 eV) peak was present on the nTi-S surface, confirming silane on the surface.

TABLE 2

Elemental composition of different surfaces obtained from the XPS survey scans.

|  | C | Ti | O | F | Others |
| --- | --- | --- | --- | --- | --- |
| Ti | 61.2 | 4 | 27.4 | 0.2 | 7.3 |
| nTi | 43.4 | 9.4 | 36.6 | 0.7 | 9.9 |
| nTi—S | 20 | 12 | 41 | 23.9 | 3.1 |

High resolution C1s spectra were obtained to further confirm the presence of silane on the surfaces (FIG. 3b). Studies have shown that surfaces exposed to ambient atmosphere has a small detectable amount of carbon, with three different chemical states (C—C(~284.8 eV), O—C=O (~288.5 eV) and C—O—C(~286.5 eV)) commonly present. High-resolution scans of Ti and nTi surfaces showed all three peaks with C—C was the dominant peak. After the silane modification, the —CF$_2$ (~292.0 eV) and —CF$_3$ (~293-294 eV) peaks were present on nTi-S surface, indicating the surface was successfully modified with silane.

As evidenced by XPS, the nTi-S surface has a high oxygen presence, and the highest ratio of oxygen to carbon of the three surfaces. Table 2 shows an oxygen to carbon ratio of about 2. The detected oxygen is believed to be present because of the partially uncoated areas of the nTi-S surface located at the bottom of the pits of the nTi-S pitted surface. Exposed oxygen that is near or at the surface can be beneficial for promoting biocompatibility (e.g., hemocompatibility), but must be at an appropriate level to maintain a proper balance with hydrophobicity.

A three-electrode electrochemical setup was used to analyze the corrosion behavior and material degradation of different surfaces. Potentiodynamic polarization tests were performed to determine the corrosion current density (I$_{corr}$), corrosion potential (E$_{corr}$) and corrosion penetration rate (CPY) using Faraday's expression. The potentiodynamic polarization (Tafel) curves for different surfaces were simulated in Ringer solution at 37° C. (FIG. 4). Each of the surfaces tend to passivate spontaneously in anodic region and no pitting corrosion was observed due to the formation of TiO$_2$ and the quick passivating nature of titanium. The corrosion rate of different surfaces followed the trend: nTi<Ti<nTi-S (Table 3). The nTi surface showed higher I$_{corr}$ and CPY compared to the Ti surface, whereas the nTi-S surface was the most corrosion resistant.

TABLE 3

Electrochemical corrosion parameter for different surfaces.

|  | Icorr (nA/cm$^2$) | Ecorr (mV) | CPY (mpy) ×10$^{-3}$ | Solution resistance, Rs (k ohm/cm$^2$) | Polarization resistance, Rp (k ohm/cm) | Constant Phase Element (×10$^{-6}$ μSs$^n$cm$^2$) | Homogeneity factor (n) |
| --- | --- | --- | --- | --- | --- | --- | --- |
| Ti | 135 | −251 | 46.25 | 1340 | 1340 | 73.56 | 0.89 |
| nTi | 413 | −386 | 141 | 2415 | 2415 | 64.80 | 0.93 |
| nTi—S | 15.8 | −302 | 5.39 | 5679 | 5679 | 36.12 | 0.94 |

Electrochemical impedance spectroscopy (EIS) was used to analyze the interface reactions of the passive layer formed on different surfaces. In this technique, impedance of the substrate/solution interface is measured over a variable frequency range. The interface reactions were modelled using electrical equivalent circuit (combination of resistors and capacitors) and simulated to replicate the processes that takes place in substrate-electrolyte interface. The results obtained from EIS were further analyzed to determine the polarization resistance (low-frequency region), solution resistance (high-frequency region), capacitance of the coating, and porosity.

Polarization resistance (Rp) is often used for calculating the corrosion rate. A Bode plot (FIG. 5a) and a Nyquist plot (FIG. 5b) show that the behavior of the nTi-S surface is different than that of Ti and nTi. The Ti, and nTi surfaces had one-time step resistive behavior at high and low frequencies, whereas capacitive behavior was seen at intermediate frequencies. However, the nTi-S surface shows three-time step resistive behavior, indicating three different interactions due to its superhydrophobic nature and the presence of multiple interfaces (Cassie-Baxter state, silane modification, and surface topography). The electrical equivalent circuits designed to fit the nTi-S surface therefore consisted of three constant phase elements (FIG. 5c).

The results indicate that polarization resistance (R$_p$) obtained after curve fitting followed the trend: <nTi<Ti<nTi-S. Thus, the higher impedance spectra shown by nTi-S reflect the high corrosion resistance and effectiveness of the silane coating on the micro-nano topography. Further, a higher n value (measure of passive layer homogeneity) arises from the CPE element (eq. 5; see Example 2 below), indicating that a relatively superior passive film was formed on the nTi-S surface with less inhomogeneities and porosity.

Mott Schottky curves ($1/C^2$ vs E) for the passive layer formed on different surfaces in ringer solution (FIG. 6) were analyzed. The Mott Schottky curves for each of the three surfaces are similar. The passive film displayed n-type behavior in the −0.5 V to −0.1 V region and dielectric behavior above −0.1 V. The calculated donor density values (using eq. 6; see Example 2 below) for all surfaces were of the order of $10^{20}/cm^3$. The results also indicate that the trend observed here is similar to the reported Mott Schottky behavior for titanium surfaces. However, the nTi-S MS curve yields a higher slope with lower donor density values compared to Ti, whereas both n-Ti had higher donor density value. This indicates a relatively superior passive film was formed on the nTi-S surface with less inhomogeneities and porosity.

Cytotoxicity of three surfaces was characterized after 2 hours of incubation with Platelet Rich Plasma (PRP). PRP of human blood—composed of white blood cells and platelets—is a simple model for the of study cytotoxicity. The three titanium surfaces showed no significant differences in lactate dehydrogenase (LDH) activity compared to positive control (100% live cells) (see FIG. 7). The LDH activity of the negative control (100% dead cells) was significantly higher compared to the positive control and the three surfaces. Thus, the modified surfaces do not induce any toxicity to blood cells.

Inhibition of *S. aureus* and *E. coli* growth in presence of different surfaces was characterized after 6, 12 and 24 hours of incubation in growth media. Compared to the control (polystyrene empty well), the Ti surface and the modified surfaces significantly inhibit *S. aureus* growth in media at each time point (FIG. 8), but do not show significant inhibition of *E. coli* growth compared to the control (empty well, no surfaces).

Adhesion and colonization of *S. aureus* and *E. coli* on different surfaces was evaluated after 6, 12 and 24 hours of incubation in growth media using fluorescence microscopy. The adhered bacteria were stained using a live (green)/dead (red) stain kit and were imaged using a fluorescence microscope. After 6 hours of *S. aureus* incubation (FIG. 9*a*), there was a significant reduction in live planktonic bacteria adhesion on the nTi-S surface compared to the Ti and nTi surfaces. After 12 hours of incubation, live planktonic bacteria had formed colonies on the surface of Ti, and nTi surfaces. In contrast, there was significant reduction in live bacteria adhesion with no colonization present on the nTi-S surface.

There was also a significantly higher number of dead bacteria on the nTi surfaces. After 24 hours of incubation, live colonized bacteria had formed on the Ti surface. Even though the nTi surface had higher live bacteria adhesion compared to nTi-S, there were no colonies present on the surface. This may be due to the nano-micro scale topography of the nTi surface, which resulted in uneven spreading of bacteria, thus preventing colonization. However, the nTi-S surface had significantly lower bacteria adhesion (>90%) compared to all the other surfaces (FIG. 9*b/c*), likely due to the combination of the superhydrophobic nature of the surface, which prevents any interaction with the growth media, as well as the negative charge on the surface, which repels bacteria cells. Thus, the nTi-S surface had significantly lower live bacteria adhesion compared to other surfaces for the entire duration of the study, proving the coating is stable.

After 6 hours of *E. coli* incubation (FIG. 10*a*), there was significantly lower live bacteria adhesion on the nTi-S surface compared to large numbers of live planktonic bacteria on the Ti and nTi surfaces. After 12 hours of incubation, higher live planktonic bacteria cells were adherent on Ti, and nTi compared to nTi-S. Smaller colonies of live bacteria cells were seen on Ti surface. However, nTi had significantly higher dead bacteria, likely due to previously mentioned surface topography. After 24 hours of incubation, live colonized bacteria were found on the Ti surface. There was a significant reduction in live bacteria adhesion on the nTi and nTi-S surfaces compared to Ti (FIG. 10*b*). There were also significantly higher dead bacteria on the nTi surface (FIG. 10*c*) compared to other surfaces. The nTi-S had significantly lower bacteria adhesion (<90%) compared to other surfaces for the entire duration of the study, demonstrating that the coating is stable and superhydrophobic, prevents interaction with the media, and repels bacteria adhesion because of its negative charge.

The visualization of bacteria morphology and biofilm formation on different surfaces was investigated to understand the interaction of bacteria cells with surface topography. As shown in FIG. 11, the morphology and biofilm formation of *S. aureus* (stained blue) and *E. coli* (stained green) on the three surfaces were evaluated after 6, 12 and 24 hours of incubation in growth media. The adhered bacteria were fixed and imaged using SEM.

After 6 hours of *S. aureus* incubation (FIG. 11*a*), the Ti surface had the highest planktonic bacteria adhesion from the media, as shown in the fluorescence images. The nTi surface and the nTi-S superhydrophobic surface both prevented bacteria adhesion. After 12 hours of incubation, the Ti surface had higher bacteria adhesion and biofilm formation compared to other surfaces, the nTi surface topography completely prevented biofilm formation and localized bacteria colonies between the micron scale structures. The nTi-S surface had a significantly lower bacteria adhesion, in accordance with the fluorescence results. After 24 hours of incubation, the Ti surface was completely covered with bacteria cells with biofilm formation. The nTi surface had bacteria cells initially adhered in the valleys of the surface topography. However, the surface prevented complete biofilm formation when compared to Ti. The nTi-S surface had significantly lower bacteria adhered on the surface, as shown in the fluorescence images.

After 6 hours of *E. coli* incubation (FIG. 11*b*), the Ti surface had highest planktonic bacteria adhesion from the media, as shown by the fluorescence images. The nTi-S surface had no bacteria adhesion. However, the nTi surface had bacteria adhesion, with disintegrated cell membranes. This may be due to the surface topography, or the titanium ions present, which is antibacterial. After 12 hours of incubation, colonized bacteria were found adherent to Ti surface. The nTi surface had lower bacteria adhered on the surface compared to Ti. However, there was significant reduction in bacteria adhesion on nTi-S surface and adhered bacteria were disintegrated. After 24 hours of incubation, the colonized bacteria had covered the Ti surface with biofilm. However, there was a significant reduction in bacterial adhesion on the nTi and nTi-S surfaces compared to the Ti surface. The nTi-S surface had significantly lower bacterial adhesion compared to the Ti and nTi surfaces.

The results described above demonstrate that the nTi-S surface is a superhydrophobic micro-nano structured titanium surface with enhanced antibacterial properties that are desirable for implantable medical devises. Implantable medical devices are commonly used to replace diseased or damaged tissues. However, bacterial infections can cause implant failure and further surgery is then required to remove or replace the implant. An implant having an anti-bacterial surface would thus be of significant benefit to patients. To this end, the inventors have developed a super-hydrophobic titania micro-nano topography surface with antibacterial properties for use with cardiovascular implant applications. The hydrothermal treatment of titanium sub-strates with sulfuric acid under controlled conditions can lead to the following chemical reactions:

$$TiO_2 + 2H_2SO_4 \rightarrow Ti(SO_4)_2 + 2H_2O \qquad \text{(eq. 1)}$$

$$Ti + 2H_2SO_4 \rightarrow Ti(SO_4)_2 + 2H_2 \qquad \text{(eq. 2)}$$

$$Ti + 2H_2O \rightarrow TiO_2 + 2H_2 \qquad \text{(eq. 3)}$$

$$Ti + H_2 \rightarrow TiH_2 \qquad \text{(eq. 4)}$$

These reactions developed a micron scale topography on nTi due to faster etching at the grain boundaries because grain boundaries have higher surface energy as a result of their disordered atomic arrangement. Additionally, nanoscale pits were visible on the grain surface due to comparatively slower etching. Thus, the SEM images indicate that hydrothermal treatment of the Ti surface provides a surface having a micro-nano topography (nTi), and that perfluorosilanating the nTi surface did not further alter its surface morphology (FIG. 1). The wettability studies showed that nTi-S surface is superhydrophobic due to the combination of nanoscale topography and a low surface energy silane coating (Table 1). This leads to formation of air pockets at the nano pits that further repel water. XPS results showed that the hydrothermal treatment increased titanium and titanium oxide on the nTi surface (Table 2). The presence of silane was verified by the increase in fluorine and the presence of carbon.

Corrosion Resistance. Metal implants are prone to corro-sion after implantation due to the physiological pH, tem-perature, and electrolytes present in body fluids. Implant corrosion leads to poor functionality, durability and adverse reactions on the tissue surrounding the implant. Hence, the corrosion behavior was studied in simulated body fluid environment (FIG. 4 and Table 3). Overall, no pitting was observed and all specimens showed spontaneous passivating nature resulting in the formation of $TiO_2$. The nTi-S surface showed superior anti-corrosion behavior compared to other specimens due to its superhydrophobic nature. However, the nTi surface did in fact show higher $I_{corr}$ and CPY compared to the Ti surface. This may be due to the hydrophilic nature of the micro-nano surface topography on nTi that increases the liquid interaction of the surface. Similarly, EIS results corroborate well with the potentiodynamic experiments and the physical nature of the specimens, wherein more time steps, relatively higher impedance spectra, and n-value was observed in the nTi-S specimen.

Although bacterial adhesion is a complex phenomenon, surface charge plays a major role in dictating the bacterial adhesion with the surface and hence it was carefully inves-tigated. Mott Schottky analysis was to analyze the surface charge of the passive layer formed on the three surfaces (FIG. 6). Surface modifications can influence surface charge by altering charge carrier density and its Fermi level. The significance of relative positioning of flat-band potential with respect to OCP is key in predicting the surface charge of different surfaces. Furthermore, a decrease in donor density helps increase corrosion resistance due to fewer oxygen vacancies and less interstitial titanium. The low donor density of nTi-S and a higher slope was observed in the Mott Schottky curve ($1/C^2$ vs E) for the nTi-S specimen, which is in good agreement with potentiodynamic and EIS results. It is therefore likely that the superior corrosion resistance of nTi-S is due the formation of a thicker passive layer and fewer defects on its surface.

Surface Charge. Surface-bacteria interactions are largely influenced by surface charge—the difference between the location of flat band potential and rest potential on a surface. The results of the surface charge investigation indicate that the surface charge is highly negative on nTi-S compared to the other surfaces. Under physiological conditions (within the pH range of 5-7), most bacteria membranes are nega-tively charged and are repelled when they interact with another negatively charged surface. The nTi-S surface, being highly negative, therefore tends to repel bacteria to a greater degree than most other surfaces. Furthermore, the superhy-drophobic nature of the nTi-S surface prevents or signifi-cantly inhibits even initial bacteria adhesion. The ability of the nTi-S surface to reduce bacteria adhesion and biofilm formation is therefore likely due to the combined effects of a repulsive negative surface charge and the superhydropho-bic nature of the surface (Table 4).

TABLE 4

Surface charge parameters of different surfaces.

|  | $E_{fb}$ (mV) | $N_d$ donor density (cm$^{-3}$) | OCP (mV) | Difference ($E_{fb}$ – OCP) |
|---|---|---|---|---|
| Ti | −525 | 3.08 | −420 | −105 |
| nTi | −627 | 11.8 | −264 | −363 |
| nTi—S | −910 | 1.03 | −136 | −774 |

Cytotoxicity. The surface of a biomedical implant can be toxic to cells. Exposure of cells to the surface of an implant surface can result in cell death due to apoptosis, necrosis, or other forms of cell damage, due to toxic properties of the surface. Lactate dehydrogenase (LDH) is a stable enzyme present in the cytoplasm of cells and after cell death. Upon cell death, LDH gets released into the cell culture superna-tant. LDH activity is therefore used as a marker for cyto-toxicity. As illustrated by FIG. 7, cytotoxicity studies showed that the nTi and nTi-S surfaces did not induce any toxicity to blood cells (platelets and leukocytes) due to its favorable surface morphology or chemistry.

Bacterial Growth Inhibition. When an implant surface is exposed to bacteria cells, the surface may inhibit the growth of bacteria present in the surrounding area prior to their adherence on the surface. Bacterial inhibition studies showed that the titanium surfaces prevented S. aureus growth compared to polystyrene well plates (FIG. 8), as the presence of $TiO_2$ on the surfaces affects S. aureus membrane permeability and inhibits the synthesis of nucleic acids, which causes reduced expression of soluble proteins, thereby inhibiting bacterial growth in the media. E. coli inhibition studies showed no significant difference. How-ever, when comparing the S. aureus with E. coli, all surfaces had lower E. coli bacterial growth during the entire duration of the study, which may be due to titanium ions preventing E. coli growth.

Inhibition of Bacterial Adhesion. After planktonic bacte-ria cells encounter an implant surface, depending on surface properties, they may adhere and proliferate and eventually form a biofilm. Once adhered, the bacteria cells will synthesize an extracellular matrix on the implant surface, resulting in irreversible attachment to the surface. After adhering, the bacteria cells proliferate and colonize, and together with their extracellular matrix, form a biofilm. Biofilm formation often renders the bacteria resistant to antibiotics. Furthermore, bacteria cells in the periphery of the biofilm can detach and migrate, thereby spreading the infection. Accordingly, the prevention of bacterial adhesion and subsequent biofilm formation on a surface is a key feature of an improved biomedical implant.

S. aureus and E. coli adhesion was evaluated at different time points to understand their growth kinetics on the surfaces (FIG. 9 and FIG. 10). S. aureus adhesion and colonization studies after 24 hours of incubation showed that the nTi-S surface had significantly lower bacteria adhesion (<90%) compared to Ti and nTi. The nTi surface had significantly higher dead bacteria. This may be due to its hydrophilic nature and higher surface energy, which attracts bacteria to the surface features and induces strain to their cell membranes, eventually rupturing and killing the bacteria. Similar trends for E. coli were observed, where the nTi-S surface had significantly lower E. coli adhesion compared to other surfaces.

Biofilm Formation. Analysis of morphology and S. aureus and E. coli biofilm formation showed, after 24 hours, significantly lower bacteria adhesion on the nTi-S surface, which completely prevented biofilm formation (FIG. 11). This is because the superhydrophobic surface repels bacterial media and the surface's negative charge prevents or discourages the bacteria from adhering, resulting in a potent antibacterial surface for cardiovascular applications.

Biomimetic Superhemophobic Titanium Surface for Cardiovascular Implant Applications.

Blood contacting titanium-based implants, such as endovascular stents and heart valve casings, is prone to thrombus formation due to complex chemical, mechanical, and electronic interactions at the surface of the implant. Hence, new titanium-based implants with improved surface properties, particularly improved blood compatibility, are urgently needed.

Even though extensive research has been carried out for enhancing implant surface interactions with blood and its component, a truly hemocompatible implant surface that can prevent blood clotting has failed to reach the clinic. Implant surface interaction with blood stimulates protein (fibrinogen and platelet) adsorption, platelet adhesion, platelet activation, and inflammatory reactions. These interactions can negatively affect implant functionality and the duration it can be maintained in a patient. To address these issues, a novel superhydrophobic surface was developed and was found to be significantly hemocompatible, corrosion resistant, and antibacterial.

Surface Topography. The topography of the three different titanium surfaces was visualized using SEM. Surface topography is an important property that determines the biological responses to a foreign material. Hydrothermal treatment alters the surface properties such as topography, chemistry, and wettability without altering the bulk properties of the titanium substrate. Results indicated that Ti surfaces were smooth and did not have any unique surface topography (FIG. 12a). nTi surfaces had microscale topography, which formed because of faster etching at the grain boundaries because grain boundaries have higher surface energy due to disordered atomic arrangement. Etching on the grain surfaces also led to the formation of nano-pits. Thus, the hydrothermal treatment led to a micro-nano topography.

After silane modification, the nTi-S surfaces did not show any significant difference in surface topography when compared to nTi surfaces.

The wettability of the three surfaces was characterized using a goniometer. Apparent contact angles ($\theta$) were measured using Milli-Q water, PRP, and whole blood (which is mostly water). Wettability can be broadly classified into three categories: hemo/hydrophobic when $\theta_w$ and $\theta_b$ are >90°, superhemo/hydrophobic when $\theta_w$ and $\theta_b$ are >150°, and hemo/hydrophilic when $\theta_w$ & $\theta_b$ are <90°.

Liquid interaction with a textured surface can adapt one of two configurations to reduce the total liquid-solid free energy, a Wenzel or a Cassie-Baxter state. In the Wenzel state, the liquid permeates into the surface topography and increases the solid-liquid interfacial area. This reduces the apparent contact angle compared to the surface without surface features. In contrast, in the meta-stable Cassie-Baxter state, liquid does not interact with surface topography, creating air pockets between the liquid and surface topography. This leads to high apparent contact angles.

The Cassie-Baxter state can be achieved with a combination of low energy surface chemistry and appropriate surface topography higher titanium oxide, as confirmed by our prior XPS results. Also, while surface oxide layers attract water molecules, the nTi-S surface is a super-hemo/hydrophobic surface in the Cassie-Baxter state due to the micro-nano topography and the presence of low energy silane on the surface. The apparent contact angle with blood was lower compared to platelet rich plasma (PRP) because blood is a denser liquid (FIG. 12b).

The phase analysis of the three surfaces was assessed using an XRD because surface crystallinity plays a major role in wettability and cellular interactions. The rutile and anatase phased of $TiO_2$ are known to be more cytocompatible and these phases were present on all three surfaces. The XRD intensity peaks at 35° (100), 32° (002), 40° (101), and 53° (102) correspond to metallic alpha phase titanium (FIG. 12c). Intensity peaks at 62° (204) correspond to the $TiO_2$ anatase phase. Intensity peaks at 27° (110) and 76° (110) correspond to the rutile phase titanium oxide ($TiO_2$). The nTi and nTi-S surfaces had a higher presence of metallic alpha phase titanium on the surface because the hydrothermal treatment removed impurities and oxide layers from those surfaces. Surface modification of nTi-S did not alter its crystal structure compared to the nTi surface.

Fibrinogen is a key protein in the development of biomaterial-induced thrombosis, promoting thrombus formation through binding of the platelet integrin receptor $\alpha IIb\beta 3$ (GPIIb/IIIa), leading to platelet immobilization, activation, and aggregation, and the precursor for fibrin formation. Fibrin is a predominant structural component in the blood clotting coagulation cascade. The size of these proteins is in the nanometer range. Nano, micro or micro-nano surface topography influences protein adsorption and alters protein conformation and spatial distribution on a surface. Protein size and confirmation, and surface topography, thus influence protein adsorption and nucleation inside the surface topography.

Fibrinogen adsorption from PRP on the three surface was measured using a commercially available enzyme linked immunoassay (ELISA) for human fibrinogen. The surface exposed PRP was analyzed to evaluate the protein content in the solution. The amount of protein adsorbed on the surface was calculated by subtracting the protein content in the positive control. Results indicate no significant difference in fibrinogen adsorption on nTi and Ti surfaces (FIG. 13). In contrast, the nTi-S surfaces had significantly lower fibrinogen adsorption compared to the nTi and Ti surfaces. This can be attributed to the lower surface energy nTi-S surface, which prevents interaction with liquid, thereby reducing protein adsorption. In addition, fibrinogen adhered to hydrophobic surfaces have a specific conformation that prevents fibrinogen fiber formation.

In the coagulation cascade, platelet and leukocyte adhesion is the step immediately following fibrinogen adsorption on the surface. Accordingly, after incubation with PRP, live cell (platelet and leukocyte) adhesion on the three surface was assessed. Activated platelets can bind to other platelets, as wells as interact with leukocytes (FIG. 14a), producing mixed aggregates. The results of FIG. 14b show that the Ti surface had significantly higher cell adhesion compared to the nTi and nTi-S surfaces. The nTi surface showed lower cell adhesion compared to the Ti surface because the surface has significantly lower surface area due to presence of nano-pits, thus preventing cell adhesion. The nTi-S surface had the lowest platelet/leukocyte adhesion because the super-hemophobic nature of the surface prevents interaction of the liquid with the nTi-S surface.

Identification of platelet and leukocytes on different surfaces was assessed after incubation with PRP by staining the cells with rhodamine phalloidin and DAPI. Platelets play a crucial role in the extrinsic pathway of the coagulation cascade while leukocytes play a crucial role in intrinsic pathway by producing anticoagulant molecules or indirectly acting on platelets. Leukocyte and platelet complex formation accelerate thrombus formation. Rhodamine phalloidin stains the cytoskeleton of both platelet and leukocytes, while DAPI stains the nucleus of leukocytes only (because platelets are a nuclear) (FIG. 14c).

The leukocyte adhesion results showed that both Ti and nTi surfaces had significantly higher leukocyte adhesion compared to nTi-S (FIG. 14d). As indicated by FIG. 14e, the Ti surface had significantly higher platelet adhesion compared to the nTi and nTi-S surfaces. The nTi surface showed lower platelet adhesion compared to the Ti surface because the micro-nano surface topography of the nTi surface had localized platelet adhesion, which prevented platelet aggregation. The nTi-S surface had the lowest platelet/leukocyte adhesion as a result of its super-hemophobic surface, which significantly inhibits and often prevents blood component interaction.

After incubation with PRP, platelet and leukocyte adhesion, activation, and complex formation on the three surfaces was visualized using SEM. When activated, platelets go through a morphology change and form dendrites and initiate aggregation. Activated platelets indirectly support leukocyte localization during thrombosis. Simultaneously, platelet-leukocyte complex formation promotes inflammation reactions. Activated platelets alter their morphology and have dendrite developed on the peripheral. As indicated by FIG. 15, the Ti surface significantly promoted platelet adhesion and activation (dendrite formation), and the planar surface assisted platelet aggregation and platelet-leukocyte formation (highlighted in purple). The nTi surface shows lower platelet adhesion and aggregate formation compared to the Ti surface. The nTi surfaces have some platelet adhesion, but the surface morphology prevented the spread of platelet aggregation and platelet activation (dendrite formation). The nTi-S surface had the least platelet adhesion, and neither platelet aggregation nor platelet activation was observed on the surface.

The hemolytic activity of different surface was assessed after incubation with erythrocytes using a commercially available hemolysis assay. Erythrocyte lysis can be induced by contact with an implant surface due to its surface chemistry, surface charge, and topography. Erythrocyte lysis induced by surface interactions leads to release of hemoglobin. Therefore, presence of hemoglobin is a marker of hemolysis. As shown by FIG. 16, hemoglobin release from erythrocytes incubated with the three surfaces was not significantly different from two FDA-approved materials, Buna N (control 1) and silicon elastomer (control 2). Hence, neither the micro-nano surface topography nor the silane chemistry induces hemolysis.

The thrombin formation of the three surfaces was assessed using a commercially available thrombin generation assay. Thrombin plays a vital role in converting fibrinogen to fibrin, which is an integral step in clot formation. Thrombin is formed from prothrombin due to activation by intrinsic and extrinsic pathways of the coagulation cascade. Thrombin generation also leads to platelet activation and inflammatory cell chemotaxis. Furthermore, thrombin has a short half-life, making its activity difficult to determine.

For the thrombin formation assessments, the surface exposed manufacturer-provided plasma was activated, and thrombin generation was measured at different time points. The results shown in FIG. 17 indicate that the thrombin generation rate was significant higher with medical steel compared to low-density polyethylene, titanium, and other modified surfaces, over a period of 4 minutes. The nTi surface had the lowest thrombin generation velocity compared to Ti, nTi-S, low density polyethylene (control 2) and medical steel (control 2) surfaces. This may be because the nTi surface is hydrophilic and there is constant thrombin generation. However, there was no significant difference between the three surfaces and the control surface in average thrombus generation over the entire duration of the study.

Complement convertase formation of different surfaces was assessed using a commercially available complement convertase assay. The coagulation cascade is a process through which thrombus is formed, divided into two categories, the intrinsic and extrinsic pathways. The intrinsic pathway (contact activation) a result of interaction between adsorbed proteins and a surface (for example, the surface of a biomedical implant). Complement activation is a part of the intrinsic inflammatory response and simultaneously influences blood clotting. Complement activation also alleviates leukocyte adhesion and activation on the implant surface.

The three surfaces were incubated with manufacturer-provided plasma and the adhered complement factors on the surface was measured. The results shown in FIG. 18 indicate that the nTi surface had significantly higher complement activation compared to other modified, low-density polyethylene (control 1) and medical steel (control 2) surfaces. However, there was no significant difference between medical steel, the Ti, and the nTi-S surfaces, and the values were in the lower spectrum of medium complement activation.

Blood clotting kinetics on the three surfaces were assessed after incubation with whole blood by measuring the amount of free hemoglobin present in the blood interacting with each surface. Previous studies evaluated the influence of proteins, enzymes, and cells individually with the modified surfaces. However, when an implant is placed inside human body, whole blood comes in contact with the surface. Accordingly, whole blood clotting kinetics were studied. After 15 minutes, 30 minutes, and 45 minutes of incubation, the three surfaces were immersed in DI water to measure the hemoglobin on live red blood cells. Red blood cells in presence of DI water rupture because of osmosis releasing hemoglobin. Thus, a higher concentration of hemoglobin in DI water indirectly indicates less blood clotting on a surface. The results shown in FIG. 19 indicate that after 45 minutes, the nTi-S surface has significantly higher hemoglobin compared to the Ti and nTi surfaces. The nTi-S surface was therefore determined to significantly prevent blood clotting. Similar trends were observed over the entire duration of study. Over time, there was steady decrease in free hemoglobin, partially due to the exposure of blood to the atmosphere.

Characteristics of the developed superhemophobic surface (nTi-S). Titanium nanostructured surfaces are currently being explored in the biomaterial industry because of titanium's excellent mechanical properties. Titanium's mechanical properties, in combination with its tissue-mimicking nanostructured surface, have shown to alleviate some surface biocompatibility issues.

The interactions between blood cells and a surface have been evaluated for various micro/nanostructures such as nanotubes, nano pores, nano fibers. Research has shown that these types of structures dictate much of the nature of the blood cell interaction with a surface. Herein is disclosed a micro-nano surface structure on titanium (FIG. 20) having a novel combination of topography and superhemophobic properties. The surface has both micro and nano structures, micron-level polygonal structures, and nanopits in the micron-level polygonal structures.

As determined by analysis of FIG. 20 and related images, the average length of the nTi-S polygonal structure was 11.06 μm (standard deviation of 4.98 μn). The average diameter (longest x-y dimension) of the nano pits was 685.85 nm (standard deviation of 180 nm). See Example 4 for additional data. This combination of micro-nanostructures with a low energy silane coating develops air pockets at the nanopits when exposed to an environment similar to that experienced by biomedical implant. Because both the air pockets and the silane coating have low energy compared to blood liquid energy, the blood is significantly repelled from the nTi-S surface, which ash been demonstrated to be superhemophobic, as discussed herein.

In summary, this disclosure provides a novel superhydrophobic surface and methods to prepare such surfaces. A simple hydrothermal treatment was used to fabricate a micro-nano surface topography on a titanium surface, and the surface was further modified with silane a provide the superhydrophobic surface. X-ray photoelectron spectroscopy results confirmed oxidation after the hydrothermal treatment and high-resolution analysis confirmed the presence of silane having peaks characteristic of the presence of carbon-fluorine on the surface. The electrochemical analysis using potentio-dynamic polarization studies showed that nTi-S had the lowest corrosion rate of the three surfaces studied, due to the combined effects of its surface topography, superhydrophobicity, and the formation of stable passive layer on the surface. In addition, electrochemical impedance spectroscopy results indicated that the nTi-S surface has less defective and thick passive film formation. Furthermore, Mott-Schottky analysis indicates that the nTi-S surface has a relatively higher negative charge compared to other surfaces.

Cytotoxicity results shows that modified surfaces (nTi and nTi-S) do not induce toxicity to blood cells. Bacteria inhibition studies showed that the surfaces inhibit S. aureus growth compared to controls. Bacteria adhesion results showed that the modified surfaces prevented bacteria colonization formation compared to Ti surfaces, and the nTi-S surface significantly reduced S. aureus and E. coli bacteria adhesion (<90%) compared to other surfaces. SEM results show that S. aureus bacteria formed a biofilm on the Ti surface at 24 hours, whereas no biofilm formed on the modified surfaces. The nTi surface adheres bacteria due to its hydrophilic nature, but the surface topography localized colonization and thus prevented biofilm formation. Remarkably, the nTi-S did not adhere any bacteria at 24 hours of incubation, due to its superhydrophobicity and negative surface charge. These results demonstrate that the superhydrophobic nTi-S surface is an antibacterial surface suitable for use with implantable medical devices.

Additionally, blood that contacts an implant is known to be highly susceptible to thrombosis. In the quest to develop a hemocompatible surface, a hydrothermal method was explored for modifying implant surfaces. The hydrothermal technique is simple and easily scalable. Titanium substrates were hydrothermally treated with sulfuric acid under a controlled atmosphere. The treatment etched the surface at micro-nano scale. The micro-nano surface topography was then coated with silane and to make the surface superhemophobic. Analysis showed that the surface did not cause any significant hemolysis compared to reference materials. Analysis of fibrinogen adhesion from PRP showed that the super-hemophobic surface adhered significantly lower fibrinogen compared to other surfaces. Reduced fibrinogen adhesion reduces or prevents platelet adhesion and activation. The three titanium surfaces described herein showed significantly lower thrombus generation kinetics compared to medical grade steel. The superhemophobic nTi-S surface did not activate higher complement, therefore it does not promote inflammation. The superhemophobic nTi-S surface also significantly prevented platelet/leukocyte adhesion compared to other surfaces studied. The superhemophobic nTi-S surface thus proved to be hemocompatible, based on its significant prevention of platelet and leukocyte adhesion.

Furthermore, whole blood clotting kinetics showed that the superhemophobic nTi-S surface was associated with significantly lower whole blood clotting after 45 minutes of incubation compared to other surfaces. The micro-nano surface coated with silane is therefore a suitable for use as a biomedical implant that contacts blood.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Preparation and Characterization of Modified Titanium Surfaces

Fabrication of nanostructured topography and surface modification on titanium. The micro-nano surface topography (nTi) was fabricated on s commercially pure titanium surface (Grade 2) using a hydrothermal process. Prior to modification, the surface (50 mm×20 mm×0.25 mm) was mechanically polished using silicon carbide sheets of different grit sizes (400, 600, 800, 100 and 1200) and cleaned with acetone in a sonicator for 10 minutes. The cleaned surface was rinsed with DI water and air dried, to provide the Ti surface.

The hydrothermal treatment was carried out by immersing the Ti surface in 0.5M sulfuric acid in a polytetrafluoroethylene (PTFE) container followed by placing the surface into a hot air oven at 80° C. for 8 hours. After the hydrothermal treatment, the surface was further cleaned with acetone in a sonicator for 10 minutes. The surface was then annealed at 300° C. for 1 hour to complete the preparation of the micro-nanostructured surface (nTi).

The micro-nanostructured surface was then etched with plasma at 200 V in 10 cm³/min of oxygen gas for 5 minutes. The surface was further modified by placing it in a closed chamber with 150 μL of silane (heptadecafluoro-1,1,2,2-tetrahydrodecyl trichlorosilane) at 120° C. for 1 hour, to provide the superhydrophobic surface (nTi-S). The treated surface was rinsed with DI water, dried with air, and stored in a desiccator until further use.

Example 2. Characterization of Adhesion and Antibiotic Properties for Bioimplant Applications Surface morphology. The surface morphology of the three titanium surfaces described herein was visualized using a JEOL 6500 field emission scanning electron microscopy (SEM). The surfaces were imaged after coating with 10 nm gold for improved conductivity. The parameters for the SEM were optimized and chosen as follows: accelerating voltage of 15 kV, working distance range: 7-12 mm, and vacuum pressure below 3×10⁻⁴ Pa. The working distance, brightness and contrast was adjusted for each surface to ensure similar quality of images. The SEM images were acquired using the secondary electron detector and back scattered detector at different magnifications ranging from 500×-5000× magnification.

Surface wettability. The surface wettability of the three titanium surfaces was characterized using a Rame-hart 260F4 goniometer. The apparent contact angle was measured using the DROPimage software 3 seconds after a 10 μL drop of DI water (polar) or hexadecane (non-polar) was placed on the surface. The advancing contact angle was measured by continuously increasing the droplet volume using a micrometer syringe. The surface energy of the three titanium surfaces was calculated using the advancing contact angles and Young's and Owens-Wendt equations.

Surface chemistry. The surface chemistry of the three titanium surfaces was characterized using a PE-5800 X-ray photoelectron spectroscopy (XPS) equipped with an Al Kα x-ray source. The overall atomic composition of different surfaces was computed by obtaining the survey scan spectra that were collected from 0 to 1100 eV. The scan was performed using a pass energy of 160 eV and a 0.05 eV step for 15 cycles. The data was analyzed using Multipak and the graphs were normalized, stacked, and plotted using Origin-Lab software. The percentage of elements present on each surface was calculated from the survey scan using the Multipak software. The high-resolution spectra scans were collected for carbon (C1s) on different surfaces. The scan was performed using a pass energy of 100 eV and a 0.05 eV step for 50 cycles. All C1 s peaks were recalibrated by shifting the maximum peak at binding energy of 284.8 eV. The peaks were fitted and plotted using OrginLab software.

Electrochemical behavior. Electrochemical behavior of different surfaces was characterized using a standard three electrode cell with a graphite rod as the counter electrode, a saturated calomel electrode (SCE) as the reference electrode, and the specimen as the working electrode using a Gamry Interface 1000 E electrochemical setup. Prior to the experiment, the surfaces were polarized cathodically at −1 V vs. SCE for 10 minutes to clean the native oxide layer. Later, OCP measurements were conducted until the system attained stable open circuit potential ($E_{OCP}$) for 3600 s.

Potentiodynamic polarization were collected at a scan rate of 0.166 mV/s from −0.4 V to +1.0 V vs $E_{OCP}$ and Tafel explorations were performed to obtain the corrosion rate in mils per year (mpy). Electrochemical impedance spectroscopy (EIS) measurements were obtained at EOCP over a frequency range of 0.01 Hz to 100 kHz with a set AC voltage amplitude of 10 mV. The electrochemical parameters obtained by electrical equivalent circuit (EEC) fitting are Rs (solution resistance), $R_p$ (polarization resistance), CPE (constant phase element), and n value (measure of passive layer homogeneity). CPE was used instead of pure capacitor to account the deviations produced by surface inhomogeneities. Impedance of CPE is given by the relation:

$$Z_{CPE} = \frac{1}{[Q(j\omega)^n]} \tag{eq. 5}$$

where Q is the Capacitance, ω is the angular frequency given by 2πf, f is the frequency, j is an imaginary root, and n was used to predict the surface heterogeneities of the formed passive layer (=1 for nearly smooth electrode).

The electronic properties of the metal in a metal-electrolyte environment were determined using Mott Schottky (M-S) analysis, a capacitive measurement technique. Mott-Schottky analysis was performed to determine the flat band potential on a potentiostatically grown oxide layer at 3V for 1000s with a negative scan from 1.5 V to −0.5 V. Gamry E-chem analyst 7.03 was used to model the electrical equivalent circuits and to analyze the data obtained. Mott-Schottky analysis was also characterized to determine the flat band potential on a potentiostatically grown oxide layer at 3 V for 1000 s with a negative scan from 0.4 V to −0.6 V.

Neglecting Helmholtz capacitance, the space charge capacitance, $C_{sc}$, can be related to the charge carrier density N (donor, $N_d$ or acceptor, $N_a$ in terms of n-type or p-type semiconductor respectively) by, $$1/C_{sc}^2=(2/q\varepsilon\varepsilon_0NA^2)/(E-E_{fb}-kT/q) \tag{eq. 6}$$

where, ε is the dielectric constant of the passive film (usually 60 for titanium), $\varepsilon_0$ is the vacuum permittivity (8.85×10-12 F/m), A is the area of the working electrode (0.5 cm²), E is the applied potential, $E_{fb}$, is the flat band potential, q is the electron charge (1.602×10⁻¹⁹ C), T is the absolute temperature (K), and k is the Boltzmann constant (1.38×10-23 J/K). N d for all specimen was determined from the slope of the respective M-S curves, whereas E f b was obtained by an extrapolation of the M-S curve to C⁻²=0.

Cytotoxicity of different surfaces. Cytotoxicity of the three titanium surfaces was evaluated using Platelet Rich Plasma (PRP). PRP was isolated from human blood as described in previous work (*Nanomedicine: Nanotechnology, Biology and Medicine.* 21 (2019) 102046). Lactate dehydrogenase (LDH) presence was evaluated using a commercially available Lactate Dehydrogenase Cytotoxicity Assay Kit. The three titanium surfaces were incubated with 300 μL Platelet Rich Plasma (PRP) for 2 hours at 37° C. in a 48 well plate. The surface exposed PRP was used to evaluate cytotoxicity of the three titanium surfaces as per the protocol given by the assay manufacturer and the absorbance was measured at 600 nm. Positive controls (PRP exposed to a blank well) and negative controls (PRP treated with Triton-X) were used to determine the maximum and minimum value of LDH.

Bacteria culture. Bacteria strains of gram-positive *Staphylococcus aureus* (*S. aureus*) and gram-negative *Escherichia coli* (*E. coli*) were used to characterize the antibacterial properties of the three titanium surfaces. Bacteria grown in an agar plate were introduced into 5 mL of trypsin soy broth (TSB) as a bacterial growth media and vortexed for 10 seconds to properly mix the bacteria within the media. This media was subsequently incubated for 6 hours at 37° C. After incubation, three dilutions (25%, 50% and 75%) of the solution were prepared to create different bacteria concentrations in a 96 well plate, and the absorbance was read at a wavelength of 562 nm in a plate reader to determine optical density. A dilution was made until the solution with an average optical density of 0.52 was obtained, indicating a concentration of $10^9$ bacteria cells/mL of TSB solution. Once the required dilution was achieved, the solution was further diluted with TSB to obtain final concentration of $10^6$ bacteria cells/mL in TSB solution.

Prior to bacteria studies, the surfaces were cut into 0.5 mm×0.5 mm samples and were cleaned by rinsing them with 500 µL of DI water and phosphate buffered saline (PBS). The surfaces were then exposed to UV light for 15 minutes for sterilization. 300 µL of bacteria solution ($10^6$ bacteria cells/ml of TSB solution) was pipetted onto each of the surfaces in 48 well plates. The well plates were incubated at 37° C. and 5% $CO_2$ for the duration of studies.

Bacteria growth inhibition by different surfaces. Bacteria inhibition on different surfaces was characterized using microplate reader by following guidelines of the Clinical and Laboratory Standards Institute using the broth microdilution method. After 6, 12 and 24 hours of incubation with bacteria solution, 100 µL of aliquot solution was used to characterize bacteria inhibition by measuring the absorbance at 600 nm. Bacteria solutions incubated in blank (polystyrene) wells were used as controls.

Bacteria adhesion and viability on different surfaces. Bacteria adhesion on the three titanium surfaces was characterized using fluorescence microscopy. After 6, 12 and 24 hours of incubation with bacteria solution, the bacteria adhesion and viability were characterized by using commercially available live/dead bacteria staining assay. In a dark environment, the surfaces were washed carefully using PBS; 500 µL of stain solution (1.5 µL/mL of propidium iodide and 1.5 µL/mL Syto 9) was then added to each well followed by incubation for 20 minutes at room temperature. After incubation, the stain solution was removed and the surfaces were rinsed with PBS twice. The surfaces were then fixed in a 3.7% formaldehyde PBS solution for 15 minutes. Finally, the fixative was removed, and the surfaces were rinsed in PBS twice before imaging under a Zeiss fluorescence microscope. Live and dead bacteria adhesion area coverage was calculated using Image J software.

Bacteria morphology. Bacteria morphology and colonization on the three titanium surfaces were characterized using SEM. After 6, 12 and 24 hours of incubation with bacteria solution, the surfaces were washed carefully using PBS. The surfaces were incubated for 45 minutes in a primary fixative solution consisting of 3% glutaraldehyde, 0.1M sodium cacodylate, and 0.1M sucrose in DI water. This was followed by further incubation for 10 minutes in a buffer solution consisting of 0.1M sodium cacodylate and 0.1M sucrose in DI water. The surfaces were then washed and dehydrated in subsequent solutions of 35%, 50%, and 70% ethanol in DI water, and 100% ethanol, for 10 minutes each. The surfaces were coated with 10 nm of gold before imaging. The SEM images were taken as described in the Surface morphology section above. The images were processed using Adobe Photoshop; *S. aureus* bacteria was colored blue and *E. coli* was colored green.

Statistical Analysis. Surface characterization techniques were repeated for at least three different samples of each surface ($n_{min}=3$). Bacteria inhibition, adhesion, and morphology studies were carried out on at least three different samples of each surface and were repeated at least three times ($n_{min}=9$). The quantitative results were analyzed using a two-way analysis of variance (ANOVA) test using the R software. The results were considered statistically significant with a p-value<0.05.

Example 3. Characterization of Hemocompatibility for Bioimplant Applications

Fabrication of micro-nanoporous surfaces. The micro-nanoporous surfaces on Grade 2 titanium foils were fabricated using the hydrothermal process and were further modified to be superhydrophobic with a silane, as described above. All modified surfaces were washed with Milli-Q water, dried with air, and stored in a sealed petri dish inside a desiccator until further use.

Surface characterization. The topography of the three titanium surfaces was visualized using a JEOL 6500 field emission scanning electron microscopy (SEM). The apparent contact angle ($\Theta^*$) of the three titanium surfaces was measured with respect to Milli-Q water, platelet rich plasma (PRP), and human blood, using a goniometer. The presence of different crystal structures on surfaces was characterized using a Bruker D8 discover DaVinci Powder X-ray diffraction (XRD) machine equipped with Cu K$\alpha$ radiation. XRD scans were collected at $\theta=1.5°$, and $2\theta$ ranges were chosen based on significant peak intensities.

Surface preparation prior to hemocompatibility studies. Surfaces were cleaned in 24-well plates with Milli-Q water and phosphate-buffered saline (PBS), each for 5 minutes. They were further sterilized by exposing to UV light inside a biosafety cabinet for 15 minutes.

Isolation of Platelet Rich Plasma (PRP) from human whole blood. Whole blood from healthy individuals who have refrained from using any medication that may affect blood clotting in past 7 days was collected in 6 mL tubes with ethylenediaminetetraacetic acid (EDTA). The procedure to collect blood was performed in accordance with the protocol approved by the Colorado State University Institutional Review Board. The procedure was also performed in compliance with the National Institutes of Health's "Guiding Principles for Ethical Research". The first tube of blood was discarded to account for formation of the platelet plug and locally activated platelets from the needle insertion. The tubes were centrifuged at 150 g at constant acceleration for 15 minutes. The tubes were allowed to rest for 15 minutes and the upper layer and buffy coat (platelet rich plasma) from the tubes were pooled prior to using with different surfaces.

Fibrinogen binding from PRP on different surfaces. Fibrinogen binding from PRP on different surfaces was measured using a commercially available enzyme linked immunoassay (ELISA) for human fibrinogen. Sterilized surfaces were incubated with PRP for 2 hours on a horizontal shaker (100 rpm) at 37° C. and 5% $CO_2$. The surface-exposed PRP was diluted 1/10,000 fold and the manufacturer provided protocol was followed to determine the fibrinogen binding on different surfaces. Absorbance of the resulting solution was measured at a 450 nm wavelength using a plate reader. Results presented are calculated after subtracting the positive control (total fibrinogen present after incubation with empty well).

Cell adhesion on different surfaces. Cell adhesion from PRP on the three titanium surfaces was visualized using fluorescence microscopy. Sterilized surfaces were incubated with PRP for 2 hours on a horizontal shaker (100 rpm) at 37° C. and 5% $CO_2$. After incubation, the PRP solution was aspirated and the surfaces were rinsed three times with PBS. The surfaces were then incubated with 5% Calcein-AM solution for 20 minutes. The stain solution was aspirated and the surfaces were rinsed three times with PBS. Surfaces were imaged using Zeiss fluorescence microscope. All images were further processed using ImageJ to calculate the surface coverage of cells.

Identification of platelet and leukocytes on different surfaces. Identification of platelet and leukocytes on the three titanium surface was visualized using fluorescence microscopy. Sterilized surfaces were incubated with PRP for 2 hours on a horizontal shaker (100 rpm) at 37° C. and 5% $CO_2$. After incubation, the PRP solution was aspirated and surfaces were rinsed three times with PBS. The surfaces were fixed using 3.7% formaldehyde and were rinsed three times with PBS. The cells were further permeabilized using 1% triton and were rinsed four times with PBS. The surfaces were then incubated with 0.05% rhodamine—phalloidin (actin) stain solution and incubated for 25 minutes. Later, 3% 4',6-diamidino-2-phenylindole (DAPI) stain solution was added and incubated for 5 minutes. The stain solution was aspirated and the surfaces were rinsed three times with PBS. Surfaces were imaged using Zeiss fluorescence microscope. All images were further processed using ImageJ to calculate the number of cells.

Platelet activation on different surfaces. Platelet activation and platelet-leukocyte complex formation on the three titanium surface was visualized using SEM. Sterilized surfaces were incubated with PRP for 2 hours on a horizontal shaker (100 rpm) at 37° C. and 5% $CO_2$. After incubation, the PRP solution was aspirated and the surfaces were rinsed three times with PBS. The surfaces were then fixed using a fixative solution containing 6% glutaraldehyde, 0.1M sodium cacodylate, and 0.1M sucrose for 45 minutes. Later, the surfaces were then incubated in a buffer solution containing 0.1M sodium cacodylate and 0.1M sucrose for 10 minutes. This was followed by dehydration of surfaces by incubation in 35%, 50%, and 70% ethanol (in DI water), and 100% ethanol, for 10 mins each. The surfaces were then air-dried and imaged using SEM.

Hemolysis of erythrocytes on different surfaces. The hemolytic activity on the three titanium surfaces was measured using a commercially available hemolysis assay kit (HaemoScan), which is in accordance the international standard ISO 10993/Part 4 and ASTM F756-08 standards to evaluate the hemocompatibility of biomaterials and medical devices. Sterilized surfaces and control surfaces (Buna-S and silicon elastomer, provided with the assay) were incubated with manufacturer provided erythrocyte suspension for 24 hours on a horizontal shaker (100 rpm) at 37° C. and 5% $CO_2$. The protocol provided by the manufacturer was followed to determine the hemolytic activity on different surfaces. Absorbance of the resulting solution was measured at 415/450/380 nm wavelengths using a plate reader.

Thrombin generation on different surfaces. Thrombin generation on the three titanium surfaces was measured using a commercially available thrombin generation assay (HaemoScan), which is in accordance the international standard ISO 10993/Part 4 to evaluate the biocompatibility of biomaterials and medical devices. Sterilized surfaces and manufacturer provided control surfaces (low-density polyethylene and medical steel, provided with the assay) were incubated with manufacturer provided plasma for 15 minutes at 37° C. The protocol provided by the manufacturer was followed to determine the maximum thrombin generation over a time interval and average thrombin generation over a period of 4 minutes from the solution incubated with different surfaces. Absorbance of the resulting solution was measured at 405 and 540 nm wavelengths using a plate reader.

Complement convertase on different surfaces. The complement activation on the three titanium surfaces was measured using a commercially available complement convertase kit (HaemoScan), which is in accordance the international standard ISO 10993/Part 4 to evaluate the biocompatibility of biomaterials and medical devices. Sterilized surfaces and manufacturer provided control surfaces (medical steel, polydimethylsiloxane, and low-density polyethylene, provided with the assay) were incubated with manufacturer provided plasma for 24 hours at 37° C. and 5% $CO_2$. The protocol provided by the manufacturer was followed to determine the complement generated due to interaction with different surfaces. Absorbance of the resulting solution was measured at a 405 nm wavelength using a plate reader.

Whole blood clotting on different surfaces. Whole blood clotting on the three titanium surfaces was assessed by indirectly measuring the amount of free hemoglobin in un-clotted blood after exposure of whole human blood to the surfaces. For this study, blood was collected in a tube without any anticoagulant coating and was used immediately after drawing. 5 μL of whole blood was pipetted on top of different surfaces and the blood was allowed to clot for up to 45 minutes. After every 15 minutes, the surfaces were evaluated for the presence of free hemoglobin. Milli-Q water was added to the surfaces and gently shaken for 30 s to lyse red blood cells that were not trapped in the clot on the surface. The absorbance of free hemoglobin released by lysed red blood cells was measured using a plate reader at 540 nm.

Statistical Analysis. Surface characterization was repeated for at least 3 different samples of each surface. SEM images and contact angle measurements were taken at 3 different locations on each sample ($n_{min}$=9). Different hemocompatibility studies were repeated at least 3 different times with blood from at least 2 heathy individuals ($n_{min}$=6). The results presented are from a single study with blood drawn from single individual because there is a significant difference in platelet count from each individual and it is therefore not appropriate to compare the absolute value. However, similar trends were observed for blood from different donors/assay kits for the obtained results, indicating reproducibility of the data. The quantitative results were analyzed using a two-way analysis of variance (ANOVA) test using the R software. Results were considered statistically significant for a p-value<0.05.

Example 4. Topography of a Representative Superhydrophobic Surface

The superhydrophobic surface (nTi-s) prepared by the method of Example 1 has both micro and nano structures, including micron-level polygonal structures. The polygonal structures (micrograins) are completely covered by nanoscale indentations, referred to herein as nanopits. The diameters of several nTi-s surface nanopits of FIG. 20 were measured and the average diameter was calculated as ~686 nm with a standard deviation of ~180 nm. Table 5 shows the individual data for the contiguous nanopits of the perfluo-rosilanated-titanium superhemophobic surface prepared by the method of Example 1.

TABLE 5

Measurements of FIG. 20 Topography: Nanopit Diameter.

| Nanopit Feature No. | Diameter (nm) |
|---|---|
| 1 | 821 |
| 2 | 552 |
| 3 | 799 |
| 4 | 253 |
| 5 | 951 |
| 6 | 626 |
| 7 | 672 |
| 8 | 944 |
| 9 | 618 |
| 10 | 742 |
| 11 | 735 |
| 12 | 516 |
| 13 | 698 |
| 14 | 387 |
| 15 | 563 |
| 16 | 618 |
| 17 | 951 |
| 18 | 704 |
| 19 | 797 |
| 20 | 770 |
| Average | 685.9 |
| Standard Deviation | 179.96 |

Additionally, the length of the polygonal structures of the nTi-S surface was measured (generally but not exclusively the longest x-y dimension; length 1), along with a measurement of the longest x-y dimension approximately perpendicular to the first measurement (length 2). The average length of the polygonal structures was 11.06 μm with a standard deviation of 4.98 Table 6 shows the measured dimensions of the contiguous micrograins of the perfluo-rosilanated-titanium, superhemophobic surface prepared by the method of Example 1.

TABLE 6

Measurements of FIG. 20 Topography: Micrograin Size.

| Micrograin Feature No. | Length 1 (μm) | Length 2 (μm) | Average Length (μm) |
|---|---|---|---|
| 1 | 21.8 | 23.6 | |
| 2 | 14.5 | 10.9 | |
| 3 | 9.45 | 3.68 | |
| 4 | 10.4 | 9.24 | |
| 5 | 10.5 | 10.5 | |
| 6 | 10.3 | 10.1 | |
| 7 | 7.29 | 5.55 | |
| 8 | 6.15 | 4.61 | |
| 9 | 14.1 | 14.9 | |
| 10 | 15.6 | 7.31 | |
| 11 | 12.6 | 10.2 | |
| Average | 12.06 | 10.06 | 11.06 |
| Standard Deviation | 4.38 | 5.55 | 4.98 |

The micro-nanostructures of the low surface energy silane coated nTi-S surface develop air pockets at the nanopits. Because the surface energy of the air pockets and silane coating are low compared to the surface energy of liquid blood, any blood in contact with the surface is significantly repelled. The nTi-S surface therefore provides a hemophobic and hemocompatible material suitable for biomedical implants.

Example 5. Surface Robustness

Sonification can be used as a cleaning process to remove impurities adhered to a surface by agitating the solution using ultrasonic energy. The nTi-S surfaces were ultrasonically cleaned in deionized (DI) water for 10 minutes at room temperature (~21° C.) in a Branson 2800 sonication bath at 40 kHz. The modified nTi-S surface proved to be highly stable during and after sonication. The applied ultrasonic cleaning process did not show any observable damage to or delamination of the surface morphology. In comparison, titanium nanotube and nanoflower surfaces, e.g., as described in U.S. Patent Publication No. 2018/0303981 (Kota), were shown to delaminate under the same sonication process conditions, wherein nanoflowers formed only on the top of the substrate and sonication caused delamination/removal of the top layer comprising the nanoflowers, resulting in a substantially untreated titanium surface.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A superhydrophobic surface comprising a perfluorosilane coating on micrograins of titania, wherein the micrograins of titania are contiguous, are surrounded by crevices, and comprise a topography of nanopits shaped by contiguous peaks and valleys, and wherein the average length of the micrograins is between 5 μm and 17 μm, and the average diameter of the nanopits is between 400 nm and 1,000 nm.

2. The superhydrophobic surface of claim 1 wherein the average length of the micrograins is about 11 μm±5 μm.

3. The superhydrophobic surface of claim 1 wherein greater than 90% of the micrograins have a length between 3 μm and 24 μm.

4. The superhydrophobic surface of claim 1 wherein the average diameter of the nanopits is 685 nm±180 nm.

5. The superhydrophobic surface of claim 1 wherein greater than 90% of the nanopits have a diameter between 505 nm and 860 nm.

6. The superhydrophobic surface of claim 1 wherein the average distance between respective centers of two adjoining nanopits is about 400 nm to about 900 nm.

7. The superhydrophobic surface of claim 1 wherein the surface energy of the superhydrophobic surface is less than 3 mJ/M$^2$.

8. The superhydrophobic surface of claim 1 wherein the advancing contact angle ($\theta_{adv}$) with respect to deionized water is greater than 160 degrees.

9. The superhydrophobic surface of claim 1 wherein the perfluorosilane is a heptadecafluoro-1,1,2,2-tetrahydrodecyl silane.

10. The superhydrophobic surface of claim 1 wherein the superhydrophobic surface has an oxygen to carbon molar ratio between 1.75:1 and 2.5:1.

11. The superhydrophobic surface of claim 1 wherein the superhydrophobic surface is an antiadhesive superhydrophobic surface of a biomedical implant.

12. The superhydrophobic surface of claim 11 wherein the biomedical implant is a cardiovascular implant, an orthopedic implant, a heart valve, an endovascular stent, or a neurovascular flow diverter, wherein the antiadhesive superhydrophobic surface of the biomedical implant is hemocompatible and reduces bacterial adhesion, fibrinogen adhesion, platelet adhesion, leukocyte adhesion, or a combination thereof, compared to a biomedical implant lacking the antiadhesive superhydrophobic surface.

13. A method for fabricating an antiadhesive superhydrophobic surface according to claim 1 comprising:

a) contacting a titanium surface and sulfuric acid under heating to form a hydrothermally treated surface;

b) annealing the hydrothermally treated surface to form an annealed surface;

c) etching the annealed surface with oxygen plasma to form an etched surface; and d) fluorinating the etched surface with a perfluorosilane to form an antiadhesive superhydrophobic surface.

14. The method of claim 13 wherein the sulfuric acid has a concentration of about 0.1% to about 99%.

15. The method of claim 13 wherein the heating of step a) is at a temperature of about 30° C. to about 500° C.

16. The method of claim 13 wherein the annealing of step b) is at a temperature of about 50° C. to about 400° C.

17. The method of claim 13 wherein the etching of step c) comprises an oxygen gas flow of about 1 $cm^3$/min to about 30 $cm^3$/min for the oxygen plasma.

18. The method of claim 13 wherein the fluorinating of step d) is performed by vapor deposition at a temperature of about 100° C. to about 150° C.

19. The method of claim 13 wherein the perfluorosilane is heptadecafluoro-1,1,2,2-tetrahydrodecyl trichlorosilane.

20. The method of claim 13 wherein the formed antiadhesive superhydrophobic surface comprises alpha-phase titanium and comprises a topography of contiguous nanopits on micro scale polygons.

\* \* \* \* \*